(12) United States Patent
Li et al.

(10) Patent No.: US 7,091,360 B2
(45) Date of Patent: Aug. 15, 2006

(54) PROCESS FOR PREPARING HETEROARYL AND UNSATURATED HETEROCYCLOALKYLMAGNESIUM REAGENTS AND USES THEREOF

(75) Inventors: Jiayao Li, Foster City, CA (US); John O. Link, San Francisco, CA (US); Colette Colladant, Bridgewater, NJ (US)

(73) Assignee: Aventis Pharma S.A., Bridgewater, NJ (US)

( * ) Notice: Subject to any disclaimer, the term of this patent is extended or adjusted under 35 U.S.C. 154(b) by 201 days.

(21) Appl. No.: 10/418,183

(22) Filed: Apr. 16, 2003

(65) Prior Publication Data

US 2004/0019218 A1 Jan. 29, 2004

Related U.S. Application Data

(60) Provisional application No. 60/373,176, filed on Apr. 16, 2002.

(51) Int. Cl.
*C07D 263/54* (2006.01)
*C07D 277/62* (2006.01)

(52) U.S. Cl. ............... 548/217; 548/152; 548/215; 546/268.1; 546/271.4

(58) Field of Classification Search ............... 548/217, 548/152, 215; 546/268.1, 271.4
See application file for complete search history.

(56) References Cited

FOREIGN PATENT DOCUMENTS

GB 824175 11/1959
WO WO 00/55144 A1 9/2000

OTHER PUBLICATIONS

Ohmoto, K. et al., "Development of orally active nonpeptidic inhibitors of human neutrophil elastase" *J. Med. Chem.* (2001); 44:1268-1285.

*Primary Examiner*—Golam M. M. Shameem
(74) *Attorney, Agent, or Firm*—Townsend and Townsend and Crew LLP

(57) ABSTRACT

The present invention is directed to a novel process for preparing heteroaryl and unsaturated heterocycloalkylmagnesium reagents that are useful in the synthesis of a variety of pharmaceuticals, in particular certain cysteine protease inhibitors.

7 Claims, No Drawings

PROCESS FOR PREPARING HETEROARYL AND UNSATURATED HETEROCYCLOALKYLMAGNESIUM REAGENTS AND USES THEREOF

CROSS-REFERENCES TO RELATED APPLICATIONS

The present application claims priority to U.S. Provisional Application Ser. No. 60/373,176, filed on Apr. 16, 2002, the disclosure of which is incorporated herein by reference in its entirety.

STATEMENT AS TO RIGHTS TO INVENTIONS MADE UNDER FEDERALLY SPONSORED RESEARCH OR DEVELOPMENT

Not applicable

REFERENCE TO A "SEQUENCE LISTING," A TABLE, OR A COMPUTER PROGRAM LISTING APPENDIX SUBMITTED ON A COMPACT DISK.

Not applicable

BACKGROUND OF THE INVENTION

1. Field of the Invention

The present invention is directed to a novel process for preparing heteroaryl and unsaturated heterocycloalkylmagnesium reagents that are useful in the synthesis of a variety of pharmaceuticals, in particular certain cysteine protease inhibitors.

2. State of the Art

Heteroaryl and unsaturated heterocycloalkylmagnesium reagents are useful in the synthesis of a variety of pharmaceuticals, such as renin inhibitors and cysteine protease inhibitors. For example, heteroarylmagnesium reagents are used in the synthesis of 1-hydroxy-1-(heteroaryl or unsaturated heterocycloalkyl)-2-N-protected-aminoethyl intermediates which are then used in the synthesis of a number of peptidic pharmaceutically active agents (see EP 0376012 which discloses the use of 1-hydroxy-1-(heteroaryl)-2-aminoethyl in the synthesis of renin inhibitors and PCT Application Publication No. WO 00/55144 and Ohmoto, K. et. al., *J. Med. Chem.* 2001, 44, 1268 which disclose the use of 1-hydroxy-1-(heteroaryl or heterocycloalkyl)-2-aminoethyl in the synthesis of protease inhibitors). At present, 1-hydroxy-1-(heteroaryl)-2-N-protected-aminoethyl intermediates used are prepared by reacting an aldehyde with a heteroarylmagnesium reagent or by assembly of the heterocyclic/heteroaryl ring. The heteroarylmagnesium reagent used in this process is prepared by first treating a heteroaryl with an organolithium reagent and then converting the resulting lithiated species into a Grignard reagent under transmetallation reaction conditions. The drawbacks of these procedures are that they require very low reaction temperatures, typically −78° C., or are not the most economical or expedient route.

In order to avoid low temperature chemistry, the heteroarylmagnesium reagent can be prepared by reacting the corresponding heteroaryl halide with magnesium turnings in the presence of an initiation mixture containing ethyl bromide and iodine crystals. The drawback of this procedure is that the initiation of the reaction is very unpredictable and the reaction is highly exothermic and hence requires appropriate set up to keep the reaction temperature under control. Additionally, this method can be subject to undesirable side reactions, such as Wurtz coupling. These drawbacks make the use of heteroaryl or unsaturated heterocycloalkylmagnesium reagents unattractive for large-scale synthesis of pharmaceuticals.

Accordingly, there is a need for a synthetic process that would be amenable to large-scale synthesis of these compounds without the limitations discussed above. The present invention fulfills this and related needs.

BRIEF SUMMARY OF THE INVENTION

The present invention is directed to a novel process for preparing heteroaryl and unsaturated heterocycloalkylmagnesium reagents and their use in the synthesis of certain cysteine protease inhibitors. As discussed above, the current synthesis of these reagents makes their use in large-scale synthesis unattractive. Applicants have surprisingly discovered that heteroaryl or unsaturated heterocycloalkylmagnesium reagents can be prepared under mild reaction conditions by treating a corresponding heteroaryl or unsaturated heterocycloalkyl compound directly with a Grignard reagent.

Accordingly, in one aspect, this invention is directed to a process of preparing a nucleophilic heteroaryl or unsaturated heterocycloalkylmagnesium reagent comprising reacting a compound of formula (I):

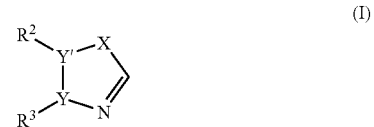

(I)

wherein:

X is —O— or —S—;

Y is nitrogen or —CR$^{3a}$—;

Y' is nitrogen or —CR$^{2a}$— provided that Y and Y' are not simultaneously nitrogen;

one of R$^2$ and R$^3$ is hydrogen, (C$_{1-6}$)alkyl, (C$_{1-6}$)alkoxy, (C$_{1-6}$)alkoxy(C$_{1-6}$)alkyl, (C$_{1-6}$)alkylthio, (C$_{5-6}$)cycloalkyl, (C$_{5-6}$)cycloalkylalkyl, halo, nitro, halo(C$_{1-3}$)alkyl, (C$_{6-12}$)aryl, heteroaryl, heterocycloalkyl, (C$_{6-12}$)aryl(C$_{1-6}$)alkyl, heteroaryl(C$_{1-6}$)alkyl, (C$_{1-6}$)alkylsulfonyl, (C$_{6-12}$)arylsulfonyl, (C$_{6-12}$)aryl(C$_{1-6}$)alkylsulfonyl, heteroarylsulfonyl, heteroaryl (C$_{1-6}$)alkylsulfonyl, aminosulfonyl, (C$_{1-6}$)alkylaminosulfonyl, (C$_{1-6}$)dialkylaminosulfonyl, —CONR$^4$R$^5$ (where R$^4$ and R$^5$ are independently of each other hydrogen, (C$_{1-6}$)alkyl, (C$_{1-6}$)alkoxy, aryl, aryl(C$_{1-6}$)alkyl, heteroaryl, heteroaryl(C$_{1-6}$)alkyl, (C$_{5-6}$)cycloalkyl, (C$_{5-6}$)cycloalkyl (C$_{1-6}$)alkyl, heterocycloalkyl, or heterocycloalkyl(C$_{1-6}$)alkyl, or R$^4$ and R$^5$ together with the nitrogen atom to which they are attached form heterocycloamino), —NHCOR$^6$ (where R$^6$ is (C$_{1-6}$)alkyl, (C$_{6-12}$)aryl, aryl(C$_{1-6}$)alkyl, heteroaryl, heteroaryl (C$_{1-6}$)alkyl, (C$_{5-6}$)cycloalkyl, (C$_{5-6}$)cycloalkyl(C$_{1-6}$)alkyl, heterocycloalkyl, or heterocycloalkyl (C$_{1-6}$)alkyl), —SO$_2$NR$^7$R$^8$ (where R$^7$ and R$^8$ are independently of each other hydrogen, (C$_{1-6}$)alkyl, (C$_{6-12}$)aryl, (C$_{6-12}$)aryl(C$_{1-6}$)alkyl, heteroaryl, heteroarylalkyl, (C$_{5-6}$)cycloalkyl, (C$_{5-6}$)cycloalkyl(C$_{1-6}$)alkyl, heterocycloalkyl, or heterocycloalkyl(C$_{1-6}$)alkyl, or R$^7$ and R$^8$ together with the nitrogen atom to which they are attached form heterocycloamino), -alkylene-CONR$^4$R$^5$ (where R$^4$ and $R^5$ are as defined above), -alkylene-NHCOR$^6$ (where $R^6$ is as defined above), or -alkylene-SO$_2$NR$^7$R$^8$ (where $R^7$ and $R^8$ are as defined above); and the other of R$^2$ and R$^3$ is hydrogen or (C$_{1-6}$)alkyl wherein within R$^2$ or R$^3$ said aryl, heteroaryl, or heterocycloalkyl is optionally substituted further with one, two, or three substituents independently selected from the group consisting of (C$_{1-6}$)alkoxy, (C$_{1-6}$)alkyl, (C$_{6-12}$)aryl(C$_{1-6}$)alkyl, halo, nitro, and halo(C$_{1-3}$)alkyl; or when Y and Y' are carbon, then R$^2$ and R$^3$ together with the atoms to which they are attached form an optionally substituted benzene, napthyl, (C$_{3-6}$)cycloalkyl, or an aromatic or non-aromatic heterocyclic ring;

R$^{2a}$ and R$^{3a}$ are independently hydrogen or alkyl; or R$^{2a}$ and R$^{3a}$ together form a covalent bond, provided that when Y or Y' is nitrogen, R$^{2a}$ and R$^3$ or R$^2$ and R$^{3a}$ together form a covalent bond;

with a Grignard reagent provided that (I) is not 1,2,4- or 1,3,4-oxadiazole.

In the context of the present invention, functional groups when present on (I) are those that are compatible with the general use of a Grignard reagent and are well known to those of skill in the art. Certain functional groups, whose presence might lead to reduced yields can be suitably protected prior to contacting the compound of formula (I) with the Grignard reagent. Again, suitable protecting groups are known to those of skill in the art and can be found in, for example, Greene and Wuts, *Protective Groups in Organic Synthesis*, 2nd ed., John Wiley & Sons, Inc. 1991.

Preferably, a compound of formula (I) where Y' is —CR$^{2a}$—.

Preferably, the Grignard reagent has an empirical formula R$^1$MgZ where R$^1$ is alkyl or optionally substituted phenyl and Z is halo, preferably Z is chloro or bromo and the reaction is carried out in a suitable organic solvent. Preferably the Grignard reagent is selected from the group consisting of n-butylmagnesium chloride, isopropylmagnesium chloride, phenylmagnesium chloride, n-butylmagnesium bromide, isopropylmagnesium bromide, or phenylmagnesium bromide. More preferably the Grignard reagent is isopropylmagnesium chloride in tetrahydrofuran.

Preferably, the reaction solvent is an ethereal organic solvent such as tetrahydrofuran and the like, or a mixture of ethereal and an aromatic organic solvent. Preferably, it is carried out in a 1:1 mixture of tetrahydrofuran and toluene.

Preferably the reaction is carried out from about −78° to about 40° C., more preferably from about −10° to about 40° C. More preferably from about −10° to about 10° C., most preferably at about −5° C.

Preferably,

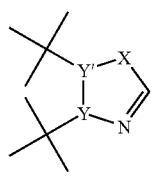

ring in (I) is 4,5-dihydrooxazole, thiazole, or oxazole wherein one of R$^2$ and R$^3$ is hydrogen or (C$_{1-4}$)alkyl and the other of R$^2$ and R$^3$ is selected from the group consisting of hydrogen, halo, (C$_{1-4}$)alkyl, (C$_{6-12}$)aryl, —CONR$^4$R$^5$ (where R$^4$ and R$^5$ are independently of each other hydrogen, (C$_{1-6}$)alkyl, (C$_{1-4}$)alkoxy, (C$_{6-12}$)aryl, (C$_{6-12}$)aryl(C$_{1-6}$)alkyl, heteroaryl, heteroaryl(C$_{1-6}$)alkyl, (C$_{5-6}$)cycloalkyl, (C$_{5-6}$)cycloalkyl(C$_{1-6}$)alkyl, heterocycloalkyl, or heterocycloalkyl(C$_{1-6}$)alkyl, or R$^4$ and R$^5$ together with the nitrogen atom to which they are attached form heterocycloamino), —SO$_2$NR$^7$R$^8$ (where R$^7$ and R$^8$ are independently of each other hydrogen, (C$_{1-6}$)alkyl, (C$_{6-12}$)aryl, (C$_{6-12}$)aryl(C$_{1-6}$)alkyl, heteroaryl, heteroaralkyl, (C$_{5-6}$)cycloalkyl, (C$_{5-6}$)cycloalkyl(C$_{1-6}$)alkyl, heterocycloalkyl, or heterocycloalkyl(C$_{1-6}$)alkyl, or R$^7$ and R$^8$ together with the nitrogen atom to which they are attached form heterocycloamino), nitro, and trifluoromethyl wherein within R$^2$ or R$^3$ said aryl, heteroaryl, or heterocycloalkyl is optionally substituted further with one, two, or three substituents independently selected from the group consisting of (C$_{1-6}$)alkoxy, (C$_{1-6}$)alkyl, (C$_{6-12}$)aryl(C$_{1-6}$)alkyl, halo, nitro, and halo(C$_{1-3}$)alkyl. Preferably, one of R$^2$ and R$^3$ is hydrogen or methyl and the other of R$^2$ and R$^3$ is selected from the group consisting of hydrogen, phenyl, phenylaminocarbonyl, benzylaminocarbonyl, aminosulfonyl, 2-phenylethylaminocarbonyl, 3-phenylpropylaminocarbonyl, aminocarbonyl, methylaminocarbonyl, 4-benzylpiperidin-1-ylcarbonyl, furan-2-ylmethylaminocarbonyl, pyridin-2-ylmethylaminocarbonyl, pyridin-3-ylmethyl-aminocarbonyl, pyridin-4-yl-methylaminocarbonyl, 2-,3-, or 4-chlorobenzylamino-carbonyl, isopropylaminocarbonyl, 1-phenylethylaminocarbonyl, N-methyl-N-benzylaminocarbonyl, pyrrolidin-1-yl-carbonyl, piperidin-1-ylcarbonyl, 1,2,3,4-tetrahydroquinolin-1-ylcarbonyl, napthyl-1-yl-methylamino-carbonyl, 1,2,3-tetrahydroindol-1-ylcarbonyl, and admant-1-ylmethylaminocarbonyl.

Preferebly, (I) is a compound where R$^2$ and R$^3$ together with the atoms to which they are attached form an optionally substituted benzene ring. Preferably, the benzene ring is optionally subsituted with (C$_{1-4}$)alkyl, halo, (C$_{1-4}$)alkoxy, (C$_{6-12}$)aryl, —CONR$^a$R$^b$ (where R$^a$ and R$^b$ are independently of each other hydrogen, (C$_{1-6}$)alkyl, (C$_{1-4}$)alkoxy, (C$_{6-12}$)aryl, (C$_{6-12}$)aryl(C$_{1-6}$)alkyl, heteroaryl, heteroaryl (C$_{1-6}$)alkyl, (C$_{5-6}$)cycloalkyl, (C$_{5-6}$)cycloalkyl-(C$_{1-6}$)alkyl, heterocycloalkyl, or heterocycloalkyl(C$_{1-6}$)alkyl, or R$^a$ and R$^b$ together with the nitrogen atom to which they are attached form heterocycloamino), —SO$_2$NR$^a$R$^b$ (where R$^a$ and R$^b$ are independently of each other hydrogen, (C$_{1-6}$)alkyl, (C$_{6-12}$)aryl, (C$_{6-12}$)aryl(C$_{1-6}$)alkyl, heteroaryl, heteroaralkyl, (C$_{5-6}$)cycloalkyl, (C$_{5-6}$)cycloalkyl(C$_{1-6}$)alkyl, heterocycloalkyl, or heterocycloalkyl(C$_{1-6}$)alkyl, or R$^a$ and R$^b$ together with the nitrogen atom to which they are attached form heterocycloamino), nitro, or trifluoromethyl.

Preferebly, (I) is benzoxazole, benzothiazole, 5-phenylbenzoxazole, 5, or 6-methoxybenzoxazole, 5-trifluorobenzoxazole, 5-nitrobenzoxazole, 5-chloro-benzoxazole, oxazolo[4,5-b]pyridine, or 5-aminosulfonylbenzoxazole, most preferably benzoxazole.

Preferably, the nucleophilic heteroaryl or unsaturated heterocycloalkylmagnesium reagent generated by the above process has the structure (Ia):

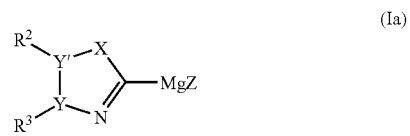

wherein X, Y, Y', R$^2$, and R$^3$ are as defined in formula (I) above, including the preferred embodiments and Z is halo, preferably chloro or bromo.

Preferebly,

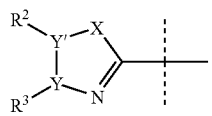

in (Ia) is benzoxazol-2-yl, benzothiazol-2-yl, 5-phenylbenzoxazol-2-yl, 5- or 6-methoxybenzoxazol-2-yl, 5-trifluorobenzoxazol-2-yl, 5-nitrobenzoxazol-2-yl, 5-chloro-benzoxazol-2-yl, oxazolo[4,5-b]pyridin-2-yl, or 5-aminosulfonylbenzoxazol-2-yl, most preferably benzoxazol-2-yl.

This invention also provides a process as described above, which further comprises reacting the nucleophilic heteroaryl or unsaturated heterocycloalkylmagnesium reagent prepared as described above (including the preferred embodiments) with an aldehyde of formula (II):

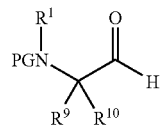

(II)

where:
PG is an amino protecting group;
$R^1$ is hydrogen or $(C_{1-6})$alkyl, or $R^1$ together with $R^{10}$ and the atoms to which they are attached form heterocycloamino;
$R^9$ is hydrogen or $(C_{1-6})$alkyl; and
$R^{10}$ is:
(i) $(C_{1-6})$alkyl optionally substituted with halo, nitro, —$SR^{11}$, —$C(O)NR^{11}R^{11}$, —$P(O)(OR^{11})OR^{11}$, —$OP(O)(OR^{11})OR^{11}$, —$S(O)R^{12}$, or —$S(O)_2R^{12}$ wherein $R^{11}$ at each occurrence independently is hydrogen, $(C_{1-6})$alkyl or halo-substituted $(C_{1-3})$alkyl and $R^{12}$ is alkyl or halo-substituted $(C_{1-3})$alkyl; or
(ii) $(C_{5-6})$cycloalkyl$(C_{2-3})$alkyl, hetero$(C_{3-6})$cycloalkyl$(C_{2-3})$alkyl, $(C_{6-12})$aryl$(C_{2-3})$alkyl or hetero$(C_{5-6})$aryl$(C_{2-3})$alkyl, wherein said cycloalkyl, heterocycloalkyl, aryl or heteroaryl optionally is substituted further with 1 to 5 radicals independently selected from the group consisting of alkyl, alkylidene, halo, halo-substituted $(C_{1-4})$alkyl, nitro, —$X^1NR^{14}C(O)OR^{14}$, —$X^1NR^{14}C(O)NR^{14}R^{14}$, —$X^1NR^{14}C(NR^{14})NR^{14}R^{14}$, —$X^1OR^{14}$, —$X^1SR^{14}$, —$X^1C(O)NR^{14}R^{14}$, —$X^1S(O)_2NR^{14}R^{14}$, —$X^1P(O)(OR^{14})OR^{14}$, —$X^1OP(O)(OR^{14})OR^{14}$, —$X^1NR^{14}C(O)R^{15}$, —$X^1S(O)R^{15}$, and —$X^1S(O)_2R^{15}$ wherein $X^1$ is a bond or $(C_{1-6})$alkyl, $R^{14}$ at each occurrence independently is hydrogen, $(C_{1-6})$alkyl or halo-substituted $(C_{1-3})$alkyl, and $R^{15}$ is $(C_{1-6})$alkyl, halo-substituted $(C_{1-3})$alkyl, or halo; or
(iii) $R^9$ and $R^{10}$ taken together with the carbon atom to which both $R^9$ and $R^{10}$ are attached form $(C_{3-8})$cycloalkylene or heterocycloalkylene, wherein said cycloalkylene or heterocycloalkylene is optionally substituted with 1 to 3 radicals independently selected from the group consisting of $(C_{1-6})$alkyl, $(C_{1-6})$alkylidene, halo, halo-substituted $(C_{1-4})$alkyl, nitro, —$X^2NR^{14}C(O)OR^{14}$, —$X^2NR^{14}C(O)NR^{14}R^{14}$, —$X^2NR^{14}C(NR^{14})NR^{14}R^{14}$, —$X^2OR^{14}$, —$X^2SR^{14}$, —$X^2C(O)NR^{14}R^{14}$, —$X^2S(O)_2NR^{14}R^{14}$, —$X^2P(O)(OR^{14})OR^{14}$, —$X^2OP(O)(OR^{14})OR^{14}$, —$X^2NR^{14}C(O)R^{15}$, —$X^2S(O)R^{15}$, and —$X^2S(O)_2R^{15}$ wherein $X^2$ is a bond or $(C_{1-6})$alkylene, $R^{14}$ at each occurrence independently is hydrogen, $(C_{1-6})$alkyl or halo-substituted $(C_{1-3})$alkyl, and $R^{15}$ is $(C_{1-6})$alkyl, halo-substituted $(C_{1-3})$alkyl, or halo; to provide a compound of formula

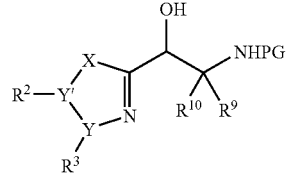

(III)

where:
X, Y, Y', PG, $R^2$, $R^3$, $R^9$, and $R^{10}$ are as defined above;
(i) optionally removing the amino protecting group;
(ii) optionally converting the compound obtained in step (i) above, to an acid addition salt;
(iii) optionally converting a salt form of a compound of formula (III) to a free base;
(iv) optionally separating individual isomers;
(v) optionally modifying any of the PG, $R^2$, $R^3$, $R^9$ and $R^{10}$ groups.

Preferably the moiety,

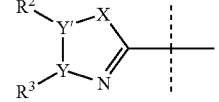

in compound (III) is as defined in the preferred embodiments for formula (I) above; $R^9$ is hydrogen or $(C_{1-6})$alkyl and $R^{10}$ is $(C_{1-6})$alkyl or $(C_{6-12})$aryl$(C_{2-3})$alkyl, or $R^9$ and $R^{10}$ taken together with the carbon atom to which both $R^9$ and $R^{10}$ are attached form $(C_{3-8})$cycloalkylene. More preferably, $R^9$ is hydrogen or methyl, more preferably hydrogen and $R^{10}$ is methyl, ethyl, propyl, butyl, phenylmethyl, or 2-phenylethyl, or $R^9$ and $R^{10}$ taken together with the carbon atom to which both $R^9$ and $R^{10}$ are attached form cyclopropylene, cyclopentylene or cyclohexylene. Even more preferably, $R^{10}$ is ethyl and the stereochemistry at the carbon atom to which $R^{10}$ is attached is (S).

Preferably, the reaction is carried out in an aromatic organic solvent such as toluene, benzene, and the like.

This invention also provides a process as described in the immediately above, additionally comprising:
removing the amino protecting group in compound (III) to provide a compound of formula (IV):

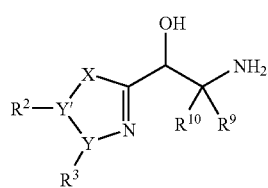

(IV)

where Y, X, $R^2$, $R^3$, $R^9$ and $R^{10}$ are as defined above (including the preferred embodiments) and optionally forming an acid addition salt; and reacting (IV) with a compound of formula (V):

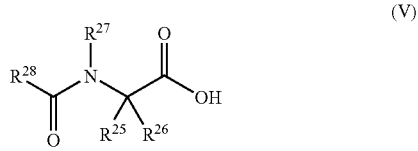

where:
$R^{25}$ and $R^{27}$ are independently of each other hydrogen or $(C_{1-6})$alkyl;
$R^{28}$ is:
(i) $(C_{1-6})$alkyl optionally substituted by cyano, halo, nitro, $-NR^{14}R^{14}$, $-NR^{14}C(O)OR^{14}$, $-NR^{14}C(O)NR^{14}R^{14}$, $-NR^{14}C(NR^{14})NR^{14}R^{14}$, $-OR^{14}$, $-SR^{14}$, $-C(O)NR^{14}R^{14}$, $-S(O)_2NR^{14}R^{14}$, $-P(O)(OR^{14})OR^{14}$, $-OP(O)(OR^{14})OR^{14}$, $-NR^{14}C(O)R^{15}$, $-S(O)R^{15}$, $-S(O)_2R^{15}$, $-C(O)R^{15}$, $-OR^{16}$, $-SR^{16}$, $-S(O)R^{16}$, $-S(O)_2R^{16}$, $-C(O)NR^{16}R^{17}$, $-NR^{16}R^{17}$, $-NR^{17}C(O)R^{16}$, $-NR^{17}C(O)OR^{16}$, $-NR^{17}C(O)NR^{16}R^{17}$ or $NR^{17}C(NR^{17})NR^{16}R^{17}$, wherein $R^{14}$ and $R^{15}$ are as defined above, $R^{16}$ is $(C_{3-12})$cycloalkyl$(C_{0-6})$alkyl, heterocycloalkyl$(C_{0-6})$alkyl, $(C_{6-12})$aryl$(C_{0-6})$alkyl, heteroaryl$(C_{0-6})$alkyl, $(C_{9-12})$bicycloaryl$(C_{0-6})$alkyl or heterobicycloaryl$(C_{0-6})$alkyl and $R^{17}$ at each occurrence independently is hydrogen or $(C_{1-6})$alkyl; or (ii) $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-6})$alkyl or hetero$(C_{8-12})$bicycloaryl$(C_{0-6})$alkyl; or (iii) $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl, wherein said cycloalkyl, heterocycloalkyl, phenyl or heteroaryl is substituted by $-R^{18}$, $-X^3OR^{18}$, $-X^3SR^{18}$, $-X^3S(O)R^{18}$, $-X^3S(O)_2R^{18}$, $-X^3C(O)R^{18}$, $-X^3C(O)OR^{18}$, $-X^3C(O)NR^{18}R^{19}$, $-X^3NR^{18}R^{19}$, $-X^3NR^{19}C(O)R^{18}$, $-X^3NR^{19}C(O)OR^{18}$, $-X^3NR^{19}C(O)NR^{18}R^{19}$ or $-X^3NR^{19}C(NR^{19})NR^{18}R^{19}$, wherein $X^3$ is a bond or $(C_{1-6})$alkylene, $R^{18}$ is $(C_{3-6})$cycloalkyl$(C_{0-6})$alkyl, hetero$(C_{3-6})$cycloalkyl$(C_{0-6})$alkyl, phenyl$(C_{0-6})$alkyl or hetero$(C_{5-6})$aryl$(C_{0-6})$alkyl and $R^{19}$ at each occurrence independently is hydrogen or $(C_{1-6})$alkyl;

wherein within $R^{28}$ any alicyclic or aromatic ring system present may be substituted further by 1 to 5 radicals independently selected from the group consisting of $(C_{1-6})$alkyl, $(C_{1-6})$alkylidene, cyano, halo, halo-substituted $(C_{1-4})$alkyl, nitro, $-X^4NR^{14}R^{14}$, $-X^4NR^{14}C(O)OR^{14}$, $-X^4NR^{14}C(O)NR^{14}R^{14}$, $-X^4NR^{14}C(NR^{14})NR^{14}R^{14}$, $-X^4OR^{14}$, $-X^4SR^{14}$, $-X^4C(O)OR^{14}$, $-X^4C(O)NR^{14}R^{14}$, $-X^4S(O)_2NR^{14}R^{14}$, $-X^4P(O)(OR^{14})OR^{14}$, $-X^4OP(O)(OR^{14})OR^{14}$, $-X^4NR^{14}C(O)R^{15}$, $-X^4S(O)R^{15}$, $-X^4S(O)_2R^{15}$ and $-X^4C(O)R^{15}$, wherein $X^4$ is a bond or $(C_{1-6})$alkylene, and $R^{14}$ and $R^{15}$ are as defined above; and $R^{26}$ is:
(i) $(C_{1-6})$alkyl optionally substituted with cyano, aryl, halo, nitro, $-NR^{14}R^{14}$, $-NR^{14}C(O)OR^{14}$, $-NR^{14}C(O)NR^{14}R^{14}$, $-NR^{14}C(NR^{14})NR^{14}R^{14}$, $-OR^{14}$, $-SR^{14}$, $-C(O)NR^{14}R^{14}$, $-S(O)_2NR^{14}R^{14}$, $-P(O)(OR^{14})OR^{14}$, $-OP(O)(OR^{14})OR^{14}$, $-NR^{14}C(O)R^{15}$, $-NR^{14}SO_2R^{15}$, $-S(O)R^{15}$, $-S(O)_2R^{15}$, $-C(O)R^{15}$, $-OR^{16}$, $-SR^{16}$, $-S(O)R^{16}$, $-S(O)_2R^{16}$, $-OC(O)R^{16}$, $-NR^{16}R^{17}$, $-NR^{17}C(O)R^{16}$, $NR^{17}C(O)OR^{16}$, $-C(O)NR^{16}R^{17}$, $-S(O)_2NR^{16}R^{17}$, $-NR^{17}C(O)NR^{16}R^{17}$ or $-NR^{17}C(NR^{17})NR^{16}R^{17}$, wherein $R^{14}$, $R^{15}$, $R^{16}$ and $R^{17}$ are as defined above, and wherein within $R^{16}$ said cycloalkyl, heterocycloalkyl, aryl, heteroaryl, bicycloaryl or heterobicycloaryl ring optionally is substituted by a group selected from $-R^{20}$, $-X^5OR^{20}$, $-X^5SR^{20}$, $-X^5S(O)R^{20}$, $-X^5S(O)_2R^{20}$, $-X^5C(O)R^{20}$, $-X^5C(O)OR^{20}$, $-X^5OC(O)R^{20}$, $-X^5NR^{20}R^{21}$, $-X^5NR^{21}C(O)R^{20}$, $-X^5NR^{21}C(O)OR^{20}$, $-X^5C(O)NR^{20}R^{21}$, $-X^5S(O)_2NR^{20}R^{21}$, $-X^5NR^{19}C(O)NR^{20}R^{21}$ and $-X^5NR^{21}C(NR^{21})NR^{20}R^{21}$, wherein $X^5$ is a bond or $(C_{1-6})$alkylene, $R^{20}$ is hydrogen or $(C_{1-6})$alkyl and $R^{21}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl; or (ii) a group selected from $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl and hetero$(C_{8-12})$polycycloaryl$(C_{0-6})$alkyl, wherein said cycloalkyl, heterocycloalkyl, aryl, heteroaryl, polycycloaryl or heterpolycycloaryl ring optionally is substituted by a group selected from $-R^{20}$, $-X^6OR^{20}$, $-X^6SR^{20}$, $-X^6S(O)R^{20}$, $-X^6S(O)_2R^{20}$, $-X^6C(O)R^{20}$, $-X^6C(O)OR^{20}$, $-X^6OC(O)R^{20}$, $-X^6NR^{20}R^{21}$, $-X^6NR^{21}C(O)R^{20}$, $-X^6NR^{21}C(O)OR^{20}$, $-X^6C(O)NR^{20}R^{21}$, $-X^6S(O)_2NR^{20}R^{21}$, $-X^6NR^{19}C(O)NR^{20}R^{21}$ and $-X^6NR^{21}C(NR^{21})NR^{20}R^{21}$, wherein $X^6$ is a bond or $(C_{1-6})$alkylene, $R^{20}$ and $R^{21}$ are as defined above;

wherein within $R^{26}$ any alicyclic or aromatic ring system present may be substituted further by 1 to 5 radicals independently selected from the group consisting of $(C_{1-6})$alkyl, $(C_{1-6})$alkylidene, cyano, halo, halo-substituted $(C_{1-4})$alkyl, nitro, $-X^7NR^{14}R^{14}$, $-X^7NR^{14}C(O)OR^{14}$, $-X^7NR^{14}C(O)NR^{14}R^{14}$, $-X^7NR^{14}C(NR^{14})NR^{14}R^{14}$, $-X^7OR^{14}$, $-X^7SR^{14}$, $-X^7C(O)OR^{14}$, $-X^7C(O)NR^{14}$ $R^{14}$, $-X^7S(O)_2NR^{14}R^{14}$, $-X^7P(O)(OR^{14})OR^{14}$, $-X^7OP(O)(OR^{14})OR^{14}$, $-X^7NR^{14}C(O)R^{15}$, $-X^7S(O)R^{15}$, $-X^7S(O)_2R^{15}$ and $-X^7C(O)R^{15}$, wherein $X^7$ is a bond or $(C_{1-6})$alkylene, and $R^{14}$ and $R^{15}$ are as defined above; or $R^{26}$ together with $R^{27}$ form trimethylene, tetramethylene or phenylene-1,2-dimethylene, optionally substituted with 1 to 3 radicals independently selected from the group consisting of $(C_{1-6})$alkyl, $(C_{1-6})$alkylidene, cyano, halo, halo-substituted $(C_{1-4})$alkyl, nitro, oxo, $-X^8NR^{14}C(O)OR^{14}$, $-X^8NR^{14}C(O)NR^{14}R^{14}$, $-X^8NR^{14}C(NR^{14})NR^{14}R^{14}$, $-X^8OR^{14}$, $-X^8SR^{14}$, $-X^8C(O)OR^{14}$, $-X^8C(O)NR^4R^{14}$, $-X^8S(O)_2NR^{14}R^{14}$, $-X^8R^{14}S(O)_2R^{15}$, $-X^8P(O)(OR^{14})OR^{14}$, $-X^8OP(O)(OR^{14})OR^{14}$, $-X^8NR^{14}C(O)R^{15}$, $-X^8S(O)R^{15}$, $-X^8S(O)_2R^{15}$ and $-X^8C(O)R^{15}$, wherein $X^8$ is a bond or $(C_{1-6})$alkylene, $R^{14}$ and $R^{15}$ are as defined above;

under coupling reaction conditions to provide a compound of formula (VI):

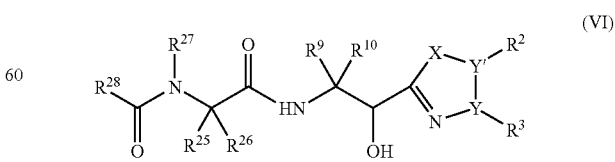

where X, Y, Y', $R^2$, $R^3$, $R^9$, $R^{10}$, $R^{25}$-$R^{28}$ are as defined above;

(i) optionally protecting the hydroxy group;
(ii) optionally converting a compound of formula (VI) to an acid addition salt;
(iii) optionally converting a salt form of a compound of formula (VI) to a free base;
(iv) optionally separating individual isomers;
(v) optionally modifying any of the X, $R^2$, $R^3$, $R^9$, $R^{10}$, and $R^{25}$—$R^{28}$ groups.

Preferably, the moiety,

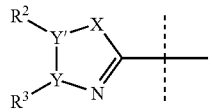

$R^9$ and $R^{10}$ are as defined in preferred embodiments above;
$R^{27}$ represents hydrogen;
$R^{25}$ represents hydrogen or methyl, preferably hydrogen; and
$R^{26}$ represents (i) $(C_{1-6})$alkyl optionally substituted with —$SR^{14}$, —$S(O)R^{14}$—$S(O)_2R^{14}$ or —$S(O)_2R^{16}$ wherein $R^{14}$ is $(C_{1-6})$alkyl and $R^{16}$ is $(C_{3-6})$cycloalkyl$(C_{1-6})$alkyl, $(C_{6-12})$aryl$(C_{0-6})$alkyl or hetero$(C_{5-12})$aryl$(C_{0-6})$alkyl; or (ii) $(C_{3-12})$cycloalkyl$(C_{0-6})$alkyl or $(C_{6-12})$aryl$(C_{0-6})$alkyl; wherein within $R^{26}$ any alicyclic or aromatic ring system present may be substituted further by 1 to 5 radicals independently selected from the group consisting of $(C_{1-6})$alkyl, $(C_{1-6})$alkylidene, cyano, halo, halo-substituted $(C_{1-4})$alkyl, nitro, —$X^5NR^{14}R^{14}$, —$X^5NR^{14}C(O)OR^{14}$, —$X^5NR^{14}C(O)NR^{14}R^{14}$, —$X^5NR^{14}C(NR^{14})NR^{14}R^{14}$, —$X^5OR^{14}$, —$X^5SR^{14}$, —$X^5C(O)OR^{14}$, —$X^5C(O)NR^{14}R^{14}$, —$X^5S(O)_2NR^{14}R^{14}$, —$X^5P(O)(OR^{14})OR^{14}$, —$X^5OP(O)(OR^4)OR^{14}$, —$X^5NR^{14}C(O)R^{15}$, —$X^5S(O)R^{15}$, —$X^5S(O)_2R^{15}$ and —$X^5C(O)R^{15}$, wherein $X^5$ is a bond or $(C_{1-6})$alkylene, $R^{14}$ at each occurrence independently is hydrogen, $(C_{1-6})$alkyl or halo-substituted $(C_{1-3})$alkyl and $R^{15}$ is $(C_{1-6})$alkyl or halo-substituted $(C_{1-3})$alkyl. Preferably $R^{26}$ is cyclohexylmethyl, isobutyl, sec-butyl, 2-fluorobenyl, benzyl, phenylethyl, 2-chlorobenzyl, 2-trifluoromethylbenzyl, 2-cyanobenzylsulfanylmethyl, benzylsulfanylmethyl, 2-cyanobenzylsulfanylmethyl, benzylsulfanylmethyl, 2-phenylsulfanylethyl, trifluoromethylbenzylsulfonylmethyl, 2-phenylsulfonylethyl, thien-3-ylmethylsulfonylmethyl, benzylsulfonylmethyl, 2-chlorobenzylsulfonylmethyl, 2-cyanobenzylsulfonylmethyl, 2-difluoromethoxybenzylsulfonylmethyl, 3,5-dimethylisoxazol-4-ylmethylsulfonylmethyl, 2-methoxybenzylsulfonylmethyl, 6-methylpyrid-2-ylmethylsulfonylmethyl, 2-methylpyrid-3-ylmethylsulfonylmethyl, pyrid-3-ylmethylsulfonylmethyl, pyrid-2-ylmethylsulfonylmethyl, 2-nitrobenzylsulfonylmethyl, pyrid-2-ylmethylsulfonylmethyl, o-tolylmethylsulfonyl-methyl, isopropylmethylsulfonylmethyl, cyclopropylmethylsulfonylmethyl, 2-trifluoromethylbenzylsulfonylmethyl. More preferably $R^{26}$ is cyclopropylmethylsulfonylmethyl or isopropylmethylsulfonylmethyl; and $R^{28}$ is methyl, azetidin-3-yl, 1-benzyloxycarbonylpiperidin-4-yl, bicyclo[2.2.2]hept-2-yl, bicyclo[2.2.1]hept-2-yl, tert-butoxy, carboxymethyl, 2-carboxyethyl, cyclohexylmethyl, 3-cyclohexylpropyl, 2-cyclohexylethyl, 2-cyclopentylethyl 6-hydroxypyrid-3-yl, 1H-imidazol-4-yl, morpholin-4-yl, 2-morpholin-4-ylethyl, naphth-1-ylmethyl, naphth-1-ylmethyl, 2-phenylethyl, piperazin-1-yl, piperidin-4-yl, pyrazin-2-yl, pyrid-3-yl, pyrid-4-yl, or tetrahydropyran-4-yl. More preferably, $R^{28}$ represents morpholin-4-yl, piperidin-4-yl, pyrazin-2-yl, pyrid-3-yl, pyrid-4-yl, or tetrahydropyran-4-yl and most preferably, morpholin-4-yl.

The deprotection conditions employed in the removal of the amino protecting group depend on the nature of the protecting group. If the group is tert-butoxycarbonyl, it is removed under acidic reaction conditions. Preferably acids are trifluoroacetic acid, hydrochloric acid, and the like. Preferably, the removal of the tert-butoxycarbonyl group is carried out by treating (III) with dioxane/HCl or trimethylsilyl chloride in an ethanolic solvent such as ethanol, isopropanol, and the like.

Preferably, the coupling reaction is carried out with a coupling agent such as benzotriazole-1-yloxytrispyrrolidino-phosphonium hexafluorophosphate (PyBOP®), O-benzotriazol-1-yl-N,N,N',N'-tetramethyluronium hexafluorophosphate (HBTU), O-(7-azabenzotriazol-1-yl)-1,1,3,3-tetramethyluronium hexafluorophosphate (HATU), or 1-hydroxybenzotriazole (HOBT) in the presence of 1-(3-dimethylaminopropyl)-3-ethylcarbodiimide hydrochloride (EDC), or 1,3-dicyclohexylcarbodiimide (DCC), a base such as N,N-diisopropylethylamine, triethylamine, or N-methylmorpholine. Suitable solvents are dichloromethane, dichloroethane, dimethylformamide, dioxane, tetrahydrofuran, or acetonitrile.

This invention also provides a process as described above additionally comprising converting a compound of formula (VI) to a compound of formula (VII):

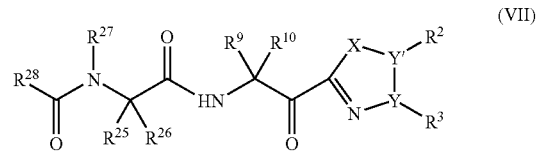

(VII)

where X, Y, Y', $R^2$, $R^3$, $R^9$, $R^{10}$, $R^{25}$–$R^{28}$ are as defined above, with a suitable oxidizing agent; and (i) optionally converting a compound of formula (VII) to an acid addition salt;
(ii) optionally converting a salt form of a compound of formula (VII) to a free base;
(iii) optionally separating individual isomers; and
(iv) optionally modifying any of the X, $R^2$, $R^3$, $R^9$, $R^{10}$, $R^{25}$–$R^{28}$ groups.

Preferably the moiety,

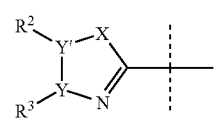

$R^{10}$, $R^{25}$–$R^{28}$ are as discussed in the preferred embodiments above.

Preferably, the oxidizing agent is selected from the group NaOCl/TEMPO®, Dess-Martin Periodinane, and the like.

The compounds of formula (VII) are cysteine protease inhibitors.

Reference to the preferred embodiments set forth above is meant to include all combinations of particular and preferred groups.

Preferably, this invention is directed to a process of preparing a compound of formula (VIIa):

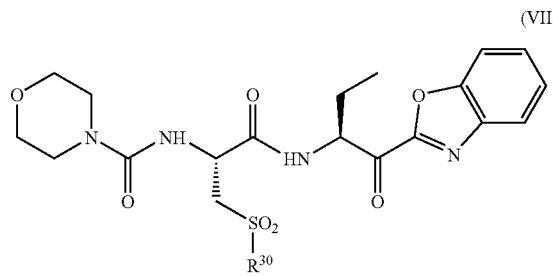
(VIIa)

wherein:

$R^{30}$ is isopropylmethyl or cyclopropylmethyl which process comprises:

(i) reacting benzoxazole with a Grignard reagent in a suitable solvent to provide a benzoxazolyl Grignard reagent;

(ii) reacting benzoxazolyl Grignard reagent obtained in Step (i) above with an aldehyde of formula (IIa):

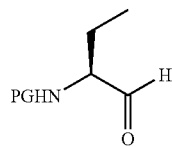
(IIa)

where PG is an amino-protecting group to provide a compound of formula (IIIa):

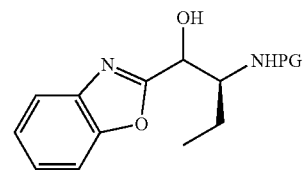
(IIIa)

(iii) deprotecting the amino group in (IIIa) with a suitable acid to provide a compound of formula (IVa) and optionally converting the free base to an acid addition salt;

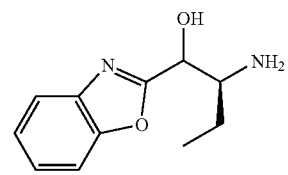
(IVa)

(iv) reacting (IVa) or an acid addition salt thereof with a compound of formula (Va):

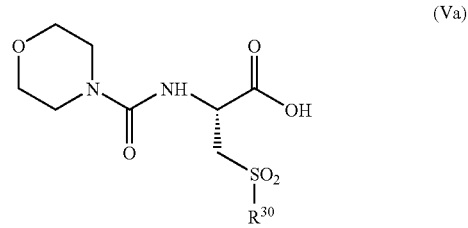
(Va)

where $R^{30}$ is cyclopropylmethyl or isopropylmethyl, under coupling reaction conditions to provide a compound of formula (VIa):

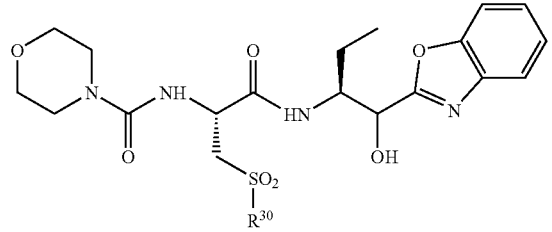
(VIa)

and;

(v) oxidizing (VIa) with a suitable oxidizing agent to provide a compound of formula (VIIa);

(vi) optionally converting a compound of formula (VIIa) to an acid addition salt;

(vii) optionally converting a salt form of a compound of formula (VIIa) to a free base; and (viii) optionally separating individual isomers.

Preferably, Step (i) is carried out at about −10° to 20° C., more preferably from about −10 to about 0° C., even more preferably at about —5° C.

Preferably, in Step (i), the Grignard reagent is n-butyl-magnesium chloride/bromide, isopropylmagnesium chloride/bromide or phenylmagnesium chloride/bromide. Preferably, the Grignard reagent is isopropylmagnesium chloride in tetrahydrofuran. Preferably, the reaction solvent is ethereal organic solvent or a mixture of ethereal and aromatic organic solvent. Preferably, the reaction is carried out in aa 1:1 mixture of tetrahydrofuran and toluene.

Preferably, in Step (ii) the reaction is carried out in aromatic organic solvent such as toluene, benzene, and the like or a mixture of ethereal and aromatic organic solvent. Preferably, the amino protecting group is tert-butoxycarbonyl, benzyl, benzyloxycarbonyl, more preferably tert-butoxycarbonyl.

Preferably, the amino protecting group in Step (iii) is removed with hydrochloric acid or trifluoroacetic acid. Preferably, the removal of the tert-butoxycarbonyl group is by treating (IIIa) with trimethylsilyl chloride in an ethanolic solvent such as ethanol, isopropanol, and the like.

Preferably, the coupling reaction in Step (iv) is carried out with a coupling agent such as benzotriazole-1-yloxytrispyrrolidino-phosphonium hexafluorophosphate (PyBOP®), O-benzotriazol-1-yl-N,N,N',N'-tetramethyluronium hexafluorophosphate (HBTU), O-(7-azabenzotriazol-1-yl)-

1,1,3,3-tetramethyluronium hexafluorophosphate (HATU), 1-hydroxybenzotriazole (HOBT), and the like. The reaction is carried out in the presence of 1-(3-dimethylaminopropyl)-3-ethylcarbodiimide hydrochloride (EDC.HCl), 1,3-dicyclohexylcarbodiimide (DCC), and the like, and a base such as N,N-diisopropylethylamine, triethylamine, N-methylmorpholine, and the like. Suitable solvents are dichloromethane, dichloroethane, dimethylformamide, dioxane, tetrahydrofuran, acetonitrile, and the like. Preferably, catalytic amount of HOBT is used.

Preferably, the oxidizing agent in Step (v) is selected from the group NaOCl/TEMPO®, Dess-Martin Periodinane, and the like.

In a second aspect, this invention is directed to 1-hydroxy-1-(heteroaryl or unsaturated heterocycloalkyl)-2-N-protected-aminoethyl intermediates of formula (III):

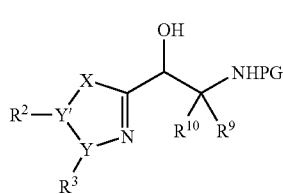

(III)

where:

X is —O— or —S—;

Y is nitrogen or —$CR^{3a}$—;

Y' is nitrogen or —$CR^{2a}$— provide that Y and Y' are not simultaneously nitrogen;

one of $R^2$ and $R^3$ is hydrogen, $(C_{1-6})$alkyl, $(C_{1-6})$alkoxy, $(C_{1-6})$alkoxy$(C_{1-6})$alkyl, amino$(C_{1-6})$alkyl, carboxy$(C_{1-6})$alkyl, hydroxy, $(C_{1-6})$alkylthio, $(C_{5-6})$cycloalkyl, $(C_{5-6})$cycloalkylalkyl, halo, nitro, halo$(C_{1-3})$alkyl, $(C_{6-12})$aryl, heteroaryl, heterocycloalkyl, $(C_{6-12})$aryl$(C_{1-6})$alkyl, heteroaryl $(C_{1-6})$alkyl, $(C_{1-6})$alkylsulfonyl, $(C_{6-12})$arylsulfonyl, $(C_{6-12})$aryl$(C_{1-6})$alkylsulfonyl, heteroarylsulfonyl, heteroaryl$(C_{1-6})$alkylsulfonyl, aminosulfonyl, $(C_{1-6})$alkylaminosulfonyl, $(C_{1-6})$dialkylaminosulfonyl, —$CONR^4R^5$ (where $R^4$ and $R^5$ are independently of each other hydrogen, $(C_{1-6})$alkyl, $(C_{1-6})$alkoxy, aryl, aryl$(C_{1-6})$alkyl, heteroaryl, heteroaryl$(C_{1-6})$alkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or $R^4$ and $R^5$ together with the nitrogen atom to which they are attached form heterocycloamino), —$NHCOR^6$ (where $R^6$ is $(C_{1-6})$ alkyl, $(C_{6-12})$aryl, aryl$(C_{1-6})$alkyl, heteroaryl, heteroaryl$(C_{1-6})$alkyl, $(C_{5-6})$cycloalkyl, $(C_{5-6})$cycloalkyl $(C_{1-6})$alkyl, heterocycloalkyl, or heterocycloalkyl$(C_{1-6})$ alkyl), —$SO_2NR^7R^8$ (where $R^7$ and $R^8$ are independently of each other hydrogen, $(C_{1-6})$alkyl, $(C_{6-12})$aryl, $(C_{6-12})$aryl $(C_{1-6})$alkyl, heteroaryl, heteroarylalkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or $R^7$ and $R^8$ together with the nitrogen atom to which they are attached form heterocycloamino), -alkylene-$CONR^4R^5$ (where $R^4$ and $R^5$ are as defined above), -alkylene-$NHCOR^6$ (where $R^6$ is as defined above), or -alkylene-$SO_2NR^7R^8$ (where $R^7$ and $R^8$ are as defined above); and the other of $R^2$ and $R^3$ is hydrogen or $(C_{1-6})$alkyl wherein within $R^2$ or $R^3$ said aryl, heteroaryl, or heterocycloalkyl is optionally substituted further with one, two, or three substituents independently selected from the group consisting of hydroxy, $(C_{1-6})$alkoxy, $(C_{1-6})$alkyl, $(C_{6-12})$aryl$(C_{1-6})$alkyl, halo, nitro, and halo$(C_{1-3})$alkyl; or $R^2$ and $R^3$ together with the atoms to which they are attached form an optionally substituted benzene or napthyl, $(C_{3-6})$cycloalkyl, or an aromatic or non-aromatic heterocyclic ring;

$R^{2a}$ and $R^{3a}$ are independently hydrogen or alkyl; or $R^{2a}$ and $R^{3a}$ together form a covalent bond, provided that when Y or Y' is nitrogen, $R^{2a}$ and $R^3$ or $R^2$ and $R^{3a}$ together form a covalent bond;

$R^9$ is hydrogen or $(C_{1-6})$alkyl; and $R^{10}$ is:

(i) $(C_{1-6})$alkyl optionally substituted with cyano, halo, nitro, —$SR^{11}$, —$C(O)OR^{11}$, —$C(O)NR^{11}R^{11}$, —$NR^{13}C(NR^{13})NR^{13}R^{13}$, —$P(O)(OR^{11})OR^{11}$, —$OP(O)(OR^{11})OR^{11}$, —$S(O)R^{12}$, —$S(O)_2R^{12}$ or —$C(O)R^{12}$, wherein $R^{11}$ at each occurrence independently is hydrogen, $(C_{1-6})$alkyl or halo-substituted $(C_{1-3})$alkyl, $R^{12}$ is alkyl or halo-substituted alkyl, and $R^{13}$ at each occurrence independently is hydrogen or $(C_{1-6})$alkyl; or (ii) $(C_{5-6})$cycloalkyl$(C_{2-3})$alkyl, hetero$(C_{3-6})$cycloalkyl $(C_{2-3})$alkyl, $(C_{6-12})$aryl$(C_{2-3})$alkyl or hetero$(C_{5-6})$aryl$(C_{2-3})$ alkyl, wherein said cycloalkyl, heterocycloalkyl, aryl or heteroaryl optionally is substituted further with 1 to 5 radicals independently selected from the group consisting of $(C_{1-6})$alkyl, alkylidene, cyano, halo, halo-substituted $(C_{1-4})$ alkyl, nitro, —$X^1NR^{14}C(O)OR^{14}$, —$X^1NR^{14}C(O)NR^{14}R^{14}$, —$X^1NR^{14}C(NR^{14})NR^{14}R^{14}$, —$X^1OR^{14}$, —$X^1SR^{14}$, —$X^1C(O)OR^{14}$, —$X^1C(O)NR^{14}R^{14}$, —$X^1S(O)_2NR^{14}R^{14}$, —$X^1P(O)(OR^{14})OR^{14}$, —$X^1OP(O)(OR^{14})OR^{14}$, —$X^1NR^{14}C(O)R^{15}$, —$X^1S(O)R^{15}$, —$X^1S(O)_2R^{15}$ and —$X^1C(O)R^{15}$, wherein $X^1$ is a bond or $(C_{1-6})$alkylene, $R^{14}$ at each occurrence independently is hydrogen, $(C_{1-6})$alkyl or halo-substituted $(C_{1-3})$alkyl, and $R^{15}$ is $(C_{1-6})$alkyl, halo-substituted $(C_{1-3})$alkyl, or halo; or (iii) $R^9$ and $R^{10}$ taken together with the carbon atom to which both $R^9$ and $R^{10}$ are attached form $(C_{3-8})$cycloalkylene or heterocycloalkylene, wherein said cycloalkylene or heterocycloalkylene is optionally substituted with 1 to 3 radicals independently selected from the group consisting of $(C_{1-6})$alkyl, $(C_{1-6})$alkylidene, cyano, halo, halo-substituted $(C_{1-4})$alkyl, nitro, —$X^2NR^{14}C(O)OR^{14}$, —$X^2NR^{14}C(O)NR^{14}R^{14}$, —$X^2NR^{14}C(NR^{14})NR^{14}R^{14}$, —$X^2OR^{14}$, —$X^2SR^{14}$, —$X^2C(O)OR^{14}$, —$X^2C(O)NR^{14}R^{14}$, —$X^2S(O)_2 NR^{14}R^{14}$, —$X^2P(O)(OR^{14})OR^{14}$, —$X^2OP(O)(OR^{14})OR^{14}$, —$X^2NR^{14}C(O)R^{15}$, —$X^2S(O)R^{15}$, —$X^2S(O)_2R^{15}$ and —$X^2C(O)R^{15}$, wherein $X^2$ is a bond or $(C_{1-6})$alkylene, $R^{14}$ and $R^{15}$ are as defined above; and individual isomers, mixture of isomers, or a salt thereof; provided that:

when X is O or S, $R^{2a}$ and $R^{3a}$ together form a covalent bond, $R^9$ is hydrogen, $R^{10}$ is $(C_{1-6})$alkyl optionally substituted with —$SR^{11}$ where $R^{11}$ is $(C_{1-6})$alkyl, and one of $R^2$ and $R^3$ is hydrogen, then the other of $R^2$ and $R^3$ is not hydrogen, alkyl, or —COR where R is amino, alkylamino or dialkylamino, or pyridin-2-ylmethylamino;

when

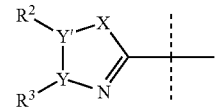

is a benzothiazol-2-yl ring, and one of $R^9$ and $R^{10}$ is hydrogen, then the other of $R^9$ and $R^{10}$ is not methyl;

when PG is benzyloxycarbonyl,

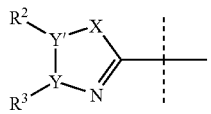

is a benzoxazol-2-yl, 4-azabenzoxazol-2-yl, or 4-, 5-, 6-, or 7-methylbenzoxazol-2-yl, and one of $R^9$ and $R^{10}$ is hydrogen, then the other of $R^9$ and $R^{10}$ is not methyl; and when PG is benzyloxycarbonyl,

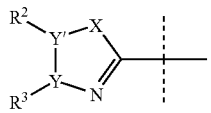

is benzoxazol-2-yl, and one of $R^9$ and $R^{10}$ is hydrogen, then the other of $R^9$ and $R^{10}$ is not isopropyl.

In the above compounds of formula (III), a preferred group of compounds is that wherein the moiety:

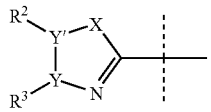

is thiazol-2-yl, 4,5-dihydrooxazol-2-yl, or oxazol-2-yl wherein one of $R^2$ and $R^3$ is hydrogen or $(C_{1-4})$alkyl and the other of $R^2$ and $R^3$ is selected from the group consisting of halo, $(C_{1-4})$alkyl, nitro, trifluoromethyl, —CONR$^4$R$^5$ (where $R^4$ and $R^5$ are independently of each other hydrogen, $(C_{1-6})$alkyl, $(C_{1-4})$alkoxy, $(C_{6-12})$aryl, $(C_{6-12})$aryl$(C_{1-6})$alkyl, heteroaryl, heteroaryl$(C_{1-6})$alkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or $R^4$ and $R^5$ together with the nitrogen atom to which they are attached form heterocycloamino), and —SO$_2$NR$^7$R$^8$ (where $R^7$ and $R^8$ are independently of each other hydrogen, $(C_{1-6})$alkyl, $(C_{6-12})$aryl, $(C_{6-12})$aryl$(C_{1-6})$alkyl, heteroaryl, heteroaralkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or $R^7$ and $R^8$ together with the nitrogen atom to which they are attached form heterocycloamino) wherein within $R^2$ or $R^3$ said aryl, heteroaryl, or heterocycloalkyl is optionally substituted further with one, two, or three substituents independently selected from the group consisting of hydroxy, $(C_{1-6})$alkoxy, $(C_{1-6})$alkyl, $(C_{6-12})$aryl$(C_{1-6})$alkyl, halo, nitro, and halo$(C_{1-3})$alkyl.

Preferably, one of $R^2$ and $R^3$ is hydrogen or methyl and the other of $R^2$ and $R^3$ is selected from the group consisting of phenyl, phenylaminocarbonyl, benzylaminocarbonyl, aminosulfonyl, 2-phenylethylaminocarbonyl, 3-phenylpropylaminocarbonyl, aminocarbonyl, methylaminocarbonyl, 4-benzylpiperidin-1-ylcarbonyl, furan-2-ylmethylaminocarbonyl, pyridin-2-ylmethylaminocarbonyl, pyridin-3-ylmethylaminocarbonyl, pyridin-4-yl-methylaminocarbonyl, 2-, 3-, or 4-chlorobenzylaminocarbonyl, isopropylaminocarbonyl, 1-phenylethylaminocarbonyl, N-methyl-N-benzylaminocarbonyl, pyrrolidin-1-yl-carbonyl, piperidin-1-ylcarbonyl, 1,2,3,4-tetrahydroquinolin-1-ylcarbonyl, napthyl-1-ylmethyl-aminocarbonyl, 2,3-dihydroindol-1-ylcarbonyl, and admant-1-ylmethylaminocarbonyl.

Another preferred group of compounds of formula (III) is that wherein $R^2$ and $R^3$ together with the carbon atoms to which they are attached form an optionally substituted benzene ring. Preferably, the benzene ring is optionally subsituted with $(C_{1-4})$alkyl, halo, $(C_{1-4})$alkoxy, $(C_{6-12})$aryl, —CONR$^a$R$^b$ (where $R^a$ and $R^b$ are independently of each other hydrogen, $(C_{1-6})$alkyl, $(C_{1-4})$alkoxy, $(C_{6-12})$aryl, $(C_{6-12})$aryl$(C_{1-6})$alkyl, heteroaryl, heteroaryl$(C_{1-6})$alkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or $R^a$ and $R^b$ together with the nitrogen atom to which they are attached form heterocycloamino), —SO$_2$NR$^1$R$^b$ (where $R^a$ and $R^b$ are independently of each other hydrogen, $(C_{1-6})$alkyl, $(C_{6-12})$aryl, $(C_{6-12})$aryl$(C_{1-6})$alkyl, heteroaryl, heteroaralkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or $R^a$ and $R^b$ together with the nitrogen atom to which they are attached form heterocycloamino), $(C_{1-4})$alkoxycarbonyl, nitro, or trifluoromethyl.

More preferably, the moiety:

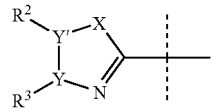

is benzoxazol-2-yl, benzothiazol-2-yl, 5-phenylbenzoxazol-2-yl, 5, or 6-methoxybenzoxazol-2-yl, 5-trifluorobenzoxazol-2-yl, 5-nitrobenzoxazol-2-yl, 5-chlorobenzoxazol-2-yl, 4-azabenzoxazol-2-yl, or 5-aminosulfonylbenzoxazol-2-yl, most preferably benzoxazol-2-yl.

Within these preferred and more preferred groups of compounds, an even more preferred group of compounds of formula (III) is that wherein:

$R^9$ is hydrogen or $(C_{1-6})$alkyl; preferably hydrogen or methyl, most preferably hydrogen; and $R^{10}$ is $(C_{1-6})$alkyl; preferably $R^{10}$ is methyl, ethyl, propyl, or butyl, or $R^9$ and $R^{10}$ together with the carbon atom to which they are attached form $(C_{3-6})$cycloalkylene, preferably $R^9$ and $R^{10}$ together with the carbon atom to which they are attached form cyclopropylene.

Most preferably, $R^{10}$ is ethyl and the stereochemistry at the carbon atom to which it is attaches is (S).

Within the above preferred groups, a more preferred group of compounds is that wherein PG is tert-butoxycarbonyl, benzyloxycarbonyl, or benzyl, more preferably tert-butoxycarbonyl.

A representative preferred compounds of formula (III) are listed below:

2-(tert-butoxycarbonyl)amino-1-benzoxazol-2-yl-2-methyl-propan-1-ol;

(S)-2-(tert-butoxycarbonyl)amino-1-benzoxazol-2-yl-hexan-1-ol;

1-(1-(tert-butoxycarbonyl)aminocyclopropyl)-1-benzoxazol-2-yl-methanol;

(S)-2-(tert-butoxycarbonyl)amino-1-benzoxazol-2-yl-propan-1-ol;

(S)-2-(tert-butoxycarbonyl)amino-1-benzoxazol-2-yl-4-methanesulfonyl-butan-1-ol;

(S)-2-(tert-butoxycarbonyl)amino-1-benzoxazol-2-yl-pentan-1-ol;

(S)-2-(tert-butoxycarbonyl)amino-1-benzoxazol-2-yl-butan-1-ol;

(S)-2-(tert-butoxycarbonyl)amino-1-benzoxazol-2-yl-4-phenylbutan-1-ol;

(S)-2-(tert-butoxycarbonyl)amino-1-(oxazol-[4,5-b]pyridin-2-yl)-butan-1-ol; and 2-(tert-butoxycarbonyl)-amino-1-benzoxazol-2-yl-3-methoxy-propan-1-ol; more preferably (S)-2-(tert-butoxycarbonyl)amino-1-benzoxazol-2-yl-propan-1-ol.

In the present invention, it is often beneficial to consider of functional group/reagent compatibility. In some embodiments, functional groups that are incompatible with particular reagents or conditions can be protected prior to reaction, using well known protecting groups. Alternatively, one of skill in the art can select equivalent reagents to be used, for example, in oxidation procedures that are mild, less deleterious to the reactants and products, or generally provide greater yields.

BRIEF DESCRIPTION OF THE DRAWINGS

DETAILED DESCRIPTION OF THE INVENTION

Definitions:

Unless otherwise stated, the following terms used in the specification and claims are defined for the purposes of this Application and have the meanings given this Section:

"Alicyclic" means a moiety characterized by arrangement of the carbon atoms in closed non-aromatic ring structures having properties resembling those of aliphatics and may be saturated or partially unsaturated with two or more double or triple bonds. Representative examples include but are not limited to cycloalkyl, cycloalkenyl, and the like.

"Aliphatic" means a moiety characterized by straight or branched saturated chain arrangement of the constituent carbon atoms. Representative examples include but are not limited to alkyl, alkylene, and the like.

"Alkyl" represented by itself means a straight or branched, saturated, aliphatic radical having one to six carbon atoms unless otherwise indicated (e.g. $(C_{1-6})$alkyl includes methyl, ethyl, propyl, isopropyl, butyl, sec-butyl, isobutyl, tert-butyl, and the like).

"Alkylthio" means the radical —SR, wherein R is alkyl as defined in this Application, having the number of carbon atoms indicated (e.g., $(C_{1-6})$alkylthio includes the radicals methylthio, ethylthio, propylthio (including all its isomeric forms), and the like).

"Alkoxy" means the radical —OR, wherein R is alkyl as defined in this Application, having the number of carbon atoms indicated (e.g., $(C_{1-6})$alkoxy includes the radicals methoxy, ethoxy, propoxy, isopropoxy, butoxy, sec-butoxy, isobutoxy, tert-butoxy, and the like).

"Alkoxycarbonyl" means the radical —C(O)OR, wherein R is alkoxy as defined in this Application.

"Alkoxyalkyl" means the radical -(alkylene)-OR, wherein R is alkyl as defined in this Application, having the number of carbon atoms indicated (e.g., $(C_{1-6})$alkoxy$(C_{1-6})$alkyl includes the radicals methoxymethyl, methoxyethyl, ethoxyethyl, and the like).

"Aminoalkyl" means the radical -(alkylene)-NRR', wherein R and R' are independently hydrogen, $(C_{1-6})$alkyl, $(C_{6-12})$aryl, $(C_{6-12})$aryl$(C_{1-6})$alkyl, heteroaryl, heteroaryl $(C_{1-6})$alkyl as defined in this Application, having the number of carbon atoms indicated (e.g., amino$(C_{1-6})$alkyl includes the radicals aminomethyl, methylaminomethyl, dimethylaminoethyl, phenylaminoethyl, and the like).

"Alkylsulfonyl" means the radical —SO$_2$R, wherein R is alkyl as defined in this Application, having the number of carbon atoms indicated (e.g., $(C_{1-6})$alkylsulfonyl includes the radicals methylsulfonyl, ethylsulfonyl, propylsulfonyl, (including all its isomeric forms), and the like).

"Alkylene", unless indicated otherwise, means a straight or branched, saturated aliphatic, divalent radical having one to six carbon atoms unless otherwise indicated, (e.g. $(C_{1-6})$ alkylene includes methylene (—CH$_2$—), ethylene (—CH$_2$CH$_2$—), trimethylene (—CH$_2$CH$_2$CH$_2$—), 2-methyltrimethylene (—CH$_2$CH(CH$_3$)CH$_2$—), tetramethylene (—CH$_2$CH$_2$CH$_2$CH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like). For example, a compound of formula I, wherein $R^{26}$ is hydrogen and $R^{12}$ taken together with $R^{27}$ forms optionally substituted trimethylene is depicted by the following illustration:

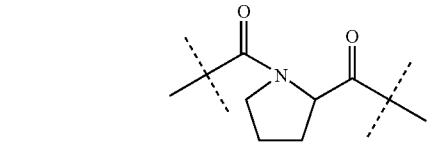

"Alkylidene" means a straight or branched saturated or unsaturated, aliphatic, divalent radical having the number of carbon atoms indicated (e.g. $(C_{1-6})$alkylidene includes methylene (=CH$^2$), ethylidene (=CHCH$_3$), isopropylidene (=C(CH$_3$)$_2$), propylidene (=CHCH$_2$CH$_3$), allylidene (=CHCH=CH$_2$), and the like).

"Amino" means the radical —NH$_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Aryl" means a monocyclic or bicyclic aromatic ring (fused or linked by a single bond) containing six to twelve carbon atoms unless otherwise indicated. For example, $(C_{6-12})$aryl as used in this Application to define R' includes phenyl, naphthyl and biphenylyl.

"Arylsulfonyl" means a radical —SO$_2$R where R is aryl as defined above. For example, $(C_{6-12})$arylsulfonyl includes phenylsulfonyl, naphthylsulfonyl, and the like.

"Arylalkyl" means an alkyl group as defined above that is substituted with an aryl group as defined above, e.g. $(C_{6-12})$aryl$(C_{1-6})$alkyl includes benzyl, phenethyl, 1-phenylethyl 3-phenylpropyl, and the like.

"Arylalkylsulfonyl" means a radical —SO$_2$R where R is arylalkyl as defined above. For example, $(C_{6-12})$aryl$(C_{1-6})$alkylsulfonyl includes benzylsulfonyl, 2-phenylethylsulfonyl, 1-phenylethylsulfonyl, naphthylmethylsulfonyl, and the like.

"Aminosulfonyl" means a radical —SO$_2$NH$_2$.

"Alkylaminosulfonyl" means a radical —SO$_2$NHR where R is alkyl as defined above. Representative examples, but are not limited to, methylaminosulfonyl, ethylaminosulfonyl, n- or isopropylaminosulfonyl, and the like.

"Aromatic" means a moiety wherein the constituent atoms make up an unsaturated ring system, all atoms in the ring system are sp2 hybridized and the total number of pi electrons is equal to 4n+2.

"Aromatic heterocyclic ring" means an aromatic ring containing five or six ring atoms wherein one or two of the ring atoms is a heteroatom selected from the group consisting of N, O or S(O)$_n$ where n is 0 to 2, the remaining ring atoms being carbon. The heterocyclic ring may be optionally fused to an aryl or heteroaryl ring. For example, compounds of formula I where R$^2$ and R$^3$ together with the carbon atoms to which they are attached form an aromatic heterocyclic ring includes rings such as:

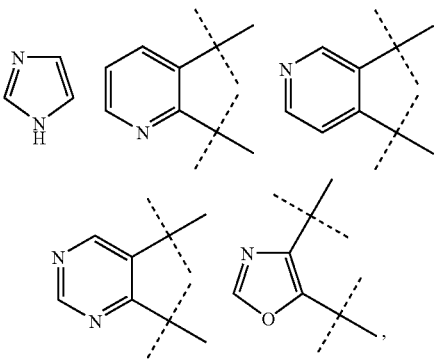

and the like.

The aromatic heterocyclic ring as defined above, is optionally substituted with one or two substituents independently selected from the group consisting of alkyl, alkoxy, trifluoromethyl, halo, haloalkoxy, nitro, aminosulfonyl, alkylaminosulfonyl, dialkylaminosulfonyl, aminoprotected group, and phenyl.

"Amino-protecting group" refers to those organic groups intended to protect nitrogen atoms against undesirable reactions during synthetic procedures. Said protecting group is readily attached and removed under mild conditions e.g., benzyl, benzyloxycarbonyl (CBZ), tert-butoxycarbonyl (BOC), trifluoroacetyl, and the like. Other suitable amino protecting groups are disclosed in Greene and Wuts, *Protective Groups in Organic Synthesis,* 2nd ed., John Wiley & Sons, Inc. 1991.

"Dialkylaminosulfonyl" means a radical —SO$^2$NRR' where R and R' are independently alkyl as defined above. Representative examples, but are not limited to, dimethylaminosulfonyl, diethylaminosulfonyl, di-n- or isopropylaminosulfonyl, methylethylamino, and the like.

"Carbamoyl" means the radical —C(O)NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Cycloalkyl" means a saturated or partially unsaturated, monocyclic ring, bicyclic ring (directly linked by a single bond or fused) or bridged polycyclic ring containing three to ten carbon atoms, unless otherwise indicated, e.g. (C$_{3-12}$) cycloalkyl includes cyclopropyl, cyclobutyl, cyclopentyl, cyclohexyl, bicyclohexylyl, bicyclo[2.2.2]octyl, adamantan-1-yl, and the like).

"Cycloalkylalkyl" means an alkyl radical as defined above that is substituted with a cycloalkyl group as defined above e.g., cyclopropylmethyl, cyclopropylethyl, cyclohexylmethyl, cyclohexylethyl, and the like.

"Cycloalkylene" means a saturated or partially unsaturated, monocyclic ring or bridged polycyclic ring containing three to eight carbon atoms, unless otherwise indicated. For example, the instance wherein R$^9$ and R$^{10}$ together with the carbon atom to which both R$^9$ and R$^{10}$ are attached form (C$_{3-8}$)cycloalkylene" includes, but is not limited to, the following:

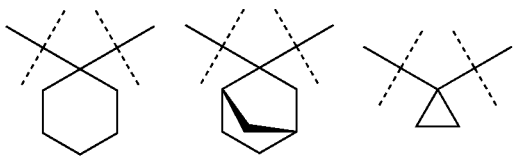

"Fused heteropolycyclic ring system" means a saturated, partially saturated or aromatic moiety containing two or more rings, wherein at least two ring member atoms of one ring are common to a second ring containing the number of ring member atoms indicated in which at least one of the ring member atoms is a heteroatom and any carbocyclic ketone, thioketone, iminoketone or substituted derivative thereof. For example, the term "a fused heteropolycyclic radical containing 8 to 14 ring member atoms" as used in this Application to define A may include acridinyl, benzofuryl, benzooxazolyl, benzothiazolyl, carbazolyl, carbolinyl, chromanyl, chromenyl, cinnolinyl, indazolyl, indolinyl, indolyl, indolizinyl, isobenzofuryl, isochromenyl, isochromanyl, isoindolinyl, isoquinolyl, naphthyridinyl, perimidinyl, phenanthridinyl, phenanthrolinyl, phenazinyl, phenothiazinyl, phenoxathiinyl, phenoxazinyl, phthalazinyl, pteridinyl, purinyl, pyrrolizinyl, quinazolinyl, quinolizinyl, quinolyl, quinoxalinyl, quinuclidinyl, xanthenyl, and the like.

"Halo" means fluoro, chloro, bromo or iodo.

"Halo-substituted alkyl" or "haloalkyl", as a group or part of a group, means alkyl as defined above, unless otherwise indicated, substituted by one or more "halo" atoms. Halo-substituted alkyl includes monohaloalkyl, dihaloalkyl, trihaloalkyl, perhaloalkyl and the like (e.g. halo-substituted (C$_{1-3}$)alkyl includes chloromethyl, diclorometyhl, difluoromethyl, trifluromethyl, 2,2,2-trifluoroethyl, perfluoroethyl, 2,2,2-trifluoro-1,1-dichloroethyl, and the like).

"Heteroaryl" means a monovalent monocyclic ring or bicyclic ring (directly linked by a single bond or fused) aromatic radical of 5 to 12 ring atoms containing one or more, preferably one, two, or three ring heteroatoms selected from N, O, or S, the remaining ring atoms being C. For example, heteroaryl as used in this Application includes benzofuryl, benzoxazolyl, benzothiazolyl, [2,4']bipyridinylyl, carbazolyl, carbolinyl, cinnolinyl, furazanyl, furyl, imidazolyl, indazolyl, indolyl, indolizinyl, isobenzofuryl, isoxazolyl, isoquinolyl, isothiazolyl, naphthyridinyl, oxazolyl, perimidinyl, pteridinyl, purinyl, pyrazinyl, pyradazinyl, pyrazolyl, pyridyl, pyrimidinyl, pyrrolizinyl, pyrrolyl, pyranyl, quinazolinyl, quinolizinyl, quinolyl, quinoxalinyl, tetrazolyl, thiazolyl, thienyl, and the like.

"Heteroarylalkyl" means an alkyl group as defined above that is substituted with a heteroaryl group as defined above, e.g. heteroaryl(C$_{1-6}$)alkyl includes pyridylmethyl, furanylmethyl, and the like.

"Heteroarylsulfonyl" means a radical —SO$_2$R where R is heteroaryl as defined above. For example, heteroarylsulfonyl includes 2-benzooxazolylsulfonyl, 2-benzothiazolylsulfonyl, 2- or 3-furylsulfonyl, 2-imidazolylsulfonyl, 2-, 3-pyridylsulfonyl, 2-pyrimidinylsulfonyl, and the like.

"Heteroarylalkylsulfonyl" means —SO$_2$R where R is heteroarylalkyl group as defined above, e.g. 2-benzooxazolylmethylsulfonyl, 2-benzothiazolylmethylsulfonyl, 2- or 3-furylmethylsulfonyl, 2-imidazolylethylsulfonyl, 2-, 3-pyridylethyl or methylsulfonyl, 2-pyrimidinyl-methyl or -ethylsulfonyl, and the like.

"Heteroatom moiety" includes —N═, —NR—, —O—, —S— and —S(O)$_2$—, wherein R is hydrogen, (C$_{1-6}$)alkyl or a protecting group.

"Heterocycloalkyl" means a saturated or partially saturated monovalent monocyclic ring or bicyclic ring (directly linked by a single bond or fused) of 3 to 12 ring atoms in which one or two ring atoms are heteroatoms selected from the group consisting of N, O, and S(O)n, where n is an integer from 0 to 2, the remaining ring atoms being C where one or two carbon atoms may optionally be replaced by a —C═O group e.g. the term heterocycloalkyl includes [1,4'] bipiperidinylyl, dihydrooxazolyl, morpholinyl, 1-morpholin-4-ylpiperidinyl, piperazinyl, piperidyl, pyrrolinyl, pyrrolidinyl, quinuclidinyl, and the like). The heterocycloalkyl may optionally be substituted with a amino protecting group. Suitable protecting groups include tert-butoxycarbonyl, benzyloxycarbonyl, benzyl, 4-methoxybenzyl, 2-nitrobenzyl, and the like. For example, a compound of formula I wherein R$^1$ is piperidin-4-ylcarbonyl may exist as either the unprotected or a protected derivative, e.g. wherein R$^1$ is 1-tert-butoxycarbonylpiperidin-4-ylcarbonyl, and both the unprotected and protected derivatives fall within the scope of the invention.

"Heterocycloalkylalkyl" means an alkyl group that is substituted with a heterocycloalkyl group as defined above. Representative examples include, but are not limited to, morpholinomethyl or ethyl, piperazin-1-ylmethyl or ethyl, piperidin-1-ylmethyl, ethyl, or propyl, and the like.

"Heterocycloalkylene" means a saturated or partially unsaturated, monocyclic ring or bridged polycyclic ring containing three to eight carbon ring atoms, unless otherwise indicated, in which one or two of the carbon ring atoms are replaced by a heteroatom selected from the group consisting of —N═, —NR—, —O—, —S— and —S(O)$_2$—, wherein R is hydrogen or (C$_{1-6}$)alkyl. For example, the instance wherein R$^9$ and R$^{10}$ together with the carbon atom to which both R$^9$ and R$^{10}$ are attached form heterocycloalkylene" includes, but is not limited to tetrahydropyranyl, piperidinyl, and the like.

"Heterocycloamino" means a-saturated monovalent cyclic group of 3 to 8 ring atoms, wherein at least one ring atom is N and optionally contains a second ring heteroatom selected from the group consisting of N, O and S(O)n (where n is an integer from 0 to 2), the remaining ring atoms being C. The heterocycloamino ring may be optionally fused to a benzene ring or it may be optionally substituted independently with one or more substituents, preferably one or two substituents, selected from (C$_{1-6}$)alkyl, halo(C$_{1-6}$)alkyl, (C$_{5-6}$)cycloalkyl, (C$_{5-6}$)cycloalkyl(C$_{1-6}$)alkyl, (C$_{6-12}$)aryl, (C$_{6-12}$)aryl(C$_{1-6}$)alkyl, heteroaryl, heteroaryl(C$_{1-6}$)alkyl, or halo. For example, a compound of formula I, wherein R$^2$ is —SO$_2$NR$^7$R$^8$ where R$^7$ and R$^8$ together with the nitrogen atom to which they are attached form heterocycloamino includes, but are not limited to groups such as:

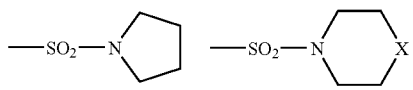

where X is C, N, O, or S and the derivatives thereof.

"Heteropolycycloaryl" means polycycloaryl, as defined herein, except one or more of the ring member carbon atoms indicated are replaced by a heteroatom moiety selected from the group consisting of —N═, —NR—, —O— and —S—, wherein R is hydrogen, (C$_{1-6}$)alkyl or a protecting group. For example, hetero(C$_{8-12}$)polycycloaryl includes 1',2'-dihydro-2H-[1,4']bipyridinylyl, imidazolinyl, indolinyl, isochromanyl, isoindolinyl, and the like.

"Heteropolycycloarylalkyl" means an alkyl group as defined above that is substituted with a heteropolycycloaryl group as defined above.

"Hydroxy" means the radical —OH. Unless indicated otherwise, the compounds of the invention containing hydroxy radicals include protected derivatives thereof. Suitable protecting groups for hydroxy moieties include benzyl and the like and both the unprotected and protected derivatives fall within the scope of the invention.

"Isomers" mean compounds of formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g. see "Advanced Organic Chemistry", 3rd edition, March, Jerry, John Wiley & Sons, New York, 1985). It is understood that the names and illustration used in this Application to describe compounds of formula I are meant to be encompassed all possible stereoisomers and any mixture, racemic or otherwise, thereof.

"Nitro" means the radical —NO$_2$.

"Nonaromatic heterocyclic ring" means a saturated or unsaturated ring containing five or six ring atoms wherein one or two of the ring atoms is a heteroatom selected from the group consisting of N, O or S(O)n where n is 0 to 2, the remaining ring atoms being carbon. The heterocyclic ring may be optionally fused to aryl or heteroaryl ring. For example, compounds of formula I where R$^2$ and R$^3$ together with the carbon atoms to which they are attached form nonaromatic heterocyclic ring includes rings such as:

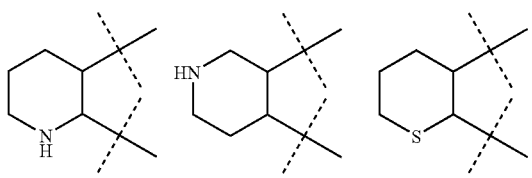

and the like.

The nonaromatic heterocyclic ring can be optionally substituted with one or two substituents independently selected from the group consisting of $(C_{1-6})$alkyl, $(C_{1-6})$alkoxy, trifluoromethyl, nitro, aminosulfonyl, $(C_{1-6})$alkylaminosulfonyl, di$(C_{1-6})$alkylaminosulfonyl, aminoprotected group, and phenyl.

"Nucleophilic" means a substance that has an electron pair available for donation. A nucleophilic reagent can undergo numerous reactions such as nucleophilic addition to an aldehyde to form an alcohol, and the like (see Jerry March, 4$^{th}$ Edition, Wiley). Therefore in order to determine whether the organomagnesium compound of this invention is nucleophilic it can be reacted with an aldehyde, such as benzaldehyde, under standard nucleophilic addition reaction conditions to determine whether it adds to the aldehyde to form a secondary alcohol. The term nucleophilic is intended as a claim limitation.

"Optionally substituted benzene" means benzene ring that is optionally substituted with one or more, preferably one or two substituents independently selected from the group consisting of $(C_{1-4})$alkyl, $(C_{1-4})$alkoxy, $(C_{6-12})$aryl, halo, —CONR$^a$R$^b$ (where R$^a$ and R$^b$ are independently of each other hydrogen, $(C_{1-6})$alkyl, $(C_{1-4})$alkoxy, $(C_{6-12})$aryl, $(C_{6-12})$aryl$(C_{1-6})$alkyl, heteroaryl, heteroaryl$(C_{1-6})$alkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or R$^a$ and R$^b$ together with the nitrogen atom to which they are attached form heterocycloamino), —SO$_2$NR$^a$R$^b$ (where R$^a$ and R$^b$ are independently of each other hydrogen, $(C_{1-6})$alkyl, $(C_{6-12})$aryl, $(C_{6-12})$aryl$(C_{1-6})$alkyl, heteroaryl, heteroaralkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or R$^a$ and R$^b$ together with the nitrogen atom to which they are attached form heterocycloamino), $(C_{1-4})$alkoxycarbonyl, nitro, or trifluoromethyl or it can be a tetrafluoro or pentafluorobenzene ring. For example, in compounds of formula I when R$^2$ and R$^3$ together with the carbon atoms to which they are attached form an optionally substituted benzene ring it means the following structure which is optionally substituted:

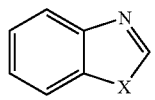

and derivatives thereof.

"Optionally substituted phenyl" means benzene ring that is optionally substituted with one or two substituents independently selected from the group consisting of halo, alkoxy or alkyl.

"Optional" or "optionally" means that the subsequently described event or circumstance may or may not occur, and that the description includes instances where the event or circumstance occurs and instances in which it does not. For example, the phrase "$(C_{1-6})$alkyl optionally substituted with cyano, halo, nitro," means that the alkyl group referred to may or may not be substituted in order to fall within the scope of the invention.

"Salt" as used herein includes acid and base addition salts. Acid addition salts are salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Base addition salts are salts which may be formed when acidic protons present are capable of reacting with inorganic or organic bases. Acceptable inorganic bases include sodium hydroxide, sodium carbonate, potassium hydroxide, ammonium hydroxide, aluminum hydroxide and calcium hydroxide. Acceptable organic bases include ethanolamine, diethanolamine, triethanolamine, tromethamine, N-methylglucamine and the like.

"Phenylene-1,2-dimethylene" means the divalent radical —CH$_2$C$_6$H$_4$CH$_2$—, wherein the methylene moieties are attached at the 1- and 2-positions of the phenylene moiety.

"Polycycloaryl" or "bicycloaryl" means a bicyclic ring assembly (directly linked by a single bond or fused) containing the number of ring member carbon atoms indicated, wherein at least one, but not all, of the fused rings comprising the radical is aromatic (e.g. $(C_{9-12})$polycycloaryl includes indanyl, indenyl, 1,2,3,4-tetrahydronaphthalenyl, 1,2-dihydronaphthalenyl, cyclohexylphenyl, phenylcyclohexyl, 2,4-dioxo-1,2,3,4-tetrahydronaphthalenyl, and the like).

"Polycycloarylalkyl" means an alkyl group as defined above that is substituted with a polycycloaryl group as defined above.

"Suitable solvent" refers to any solvent, preferably organic solvent" which does not interact with starting materials, reagents, intermediates or products in a manner which adversely affects the reaction or the yield of the desired product. Further, the term reaction inert solvent or suitable solvent may refer to a single, dual or multiple solvent systems depending upon the nature of the reaction and the solubility of the substrate and/or reagents being disclosed.

General Synthetic Sheme

Compounds of formula, (III), and (VII) can be prepared by methods described below.

Processes for Making Compounds of Formula (III)

Compounds of formula (III) where X, Y, PG, R$^2$, R$^3$, R$^9$ and R$^{10}$ are as defined in the Summary of the Invention can be prepared by proceeding as in the following Scheme 1 below:

Scheme 1

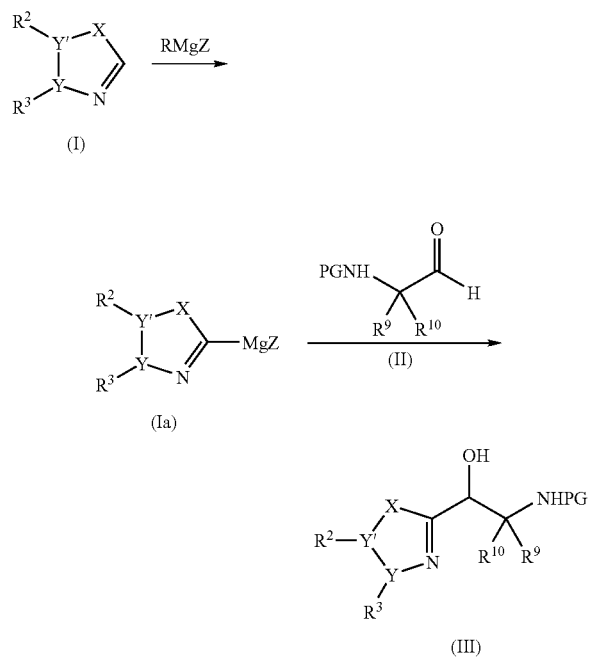

Treatment of a compound a heteroaryl or unsaturated heterocycloalkyl compound of formula (I) with a Grignard reagent, preferably a Grignard reagent of the formula RMgZ where R is alkyl or optionally substituted phenyl, preferably n-butyl, isopropyl, or phenyl and Z is halo, preferably chloro or bromo provides a heteroaryl or unsaturated heterocycloalkyl Grignard reagent respectively, of formula (Ia). The reaction is typically carried out in an ethereal organic solvent such as tetrahydrofuran, diethyl ether, dioxane, and the like, preferably tetrahydrofuran, or a mixture of ethereal and aromatic organic solvent at a temperature from about −78° to about 40° C. Preferably, the reaction is carried out from about −10° C. to about 40° C., more preferably from about −10° to about 10° C. The reaction typically requires an hour to complete. Once the reaction is complete, an aldehyde of formula (II) where PG, $R^9$ and $R^{10}$ are as defined in the Summary of the Invention is added to the reaction mixture to provide a compound of formula (III) after treatment with an aqueous acid or buffer. Preferably, PG is tert-butyoxycarbonyl, benzyloxycarbonyl, or benzyl, more preferably tert-butoxycarbonyl. The nucleophilic additon reaction is typically carried out from about −10° C. to about room temperature. The term "complete" as used herein means that there is no further appreciable conversion of starting material to the desired product as determined by traditional means such as thin layer chromatograph, NMR, HPLC, and the like. Compounds of formula (I) and (II) are either commercially available or they can be prepared by methods well known in the art.

Processes for Making Compounds of Formula (VII)

Compounds of formula (VII) where X, Y, $R^2$, $R^3$, $R^9$, $R^{10}$, and $R^{25}$–$R^{28}$ are as defined in the Summary of the Invention can be prepared as shown in Scheme 2 below.

Scheme 2

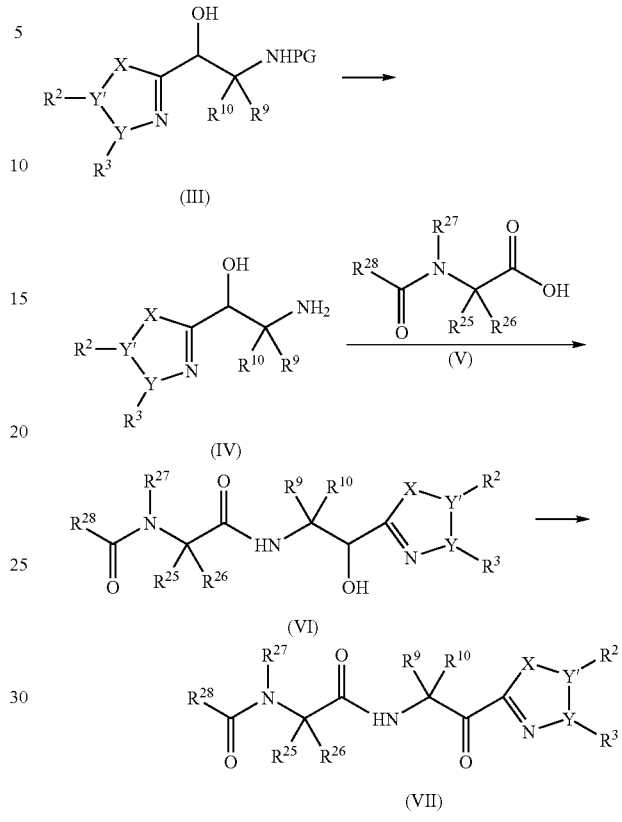

Removal of the amino protecting group in the compound of formula (III) provides a compound of formula (IV). The reaction conditions employed for removal the amino protecting group depends on the nature of the protecting group. For example, if the protecting group is tert-butoxycarbonyl, it is removed under acid reaction conditions. Suitable acids are trifluoroacetic acid, hydrochloric acid, trimethylsilane in alcoholic organic solvent, and the like. If the protecting group is benzyl it is removed under catalytic hydrogenation reaction conditions. Suitable catalyst are palladium, platinum, rodium based catalysts and others known in the art. Other suitable reaction conditions for their removal can be found in T. W. Greene, *Protecting Groups in Organic Synthesis*, John Wiley & Sons, Inc. 1981. The reaction is carried out in an inert organic solvent methylene chloride, tetrahydrofuran, dioxane, dimethylformamide, and the like.

Reaction of a compound of formula (IV) with an acid of formula (V) provides a compound of formula (VI). The reaction is carried out under suitable coupling reaction conditions. Typically, the reaction is carried out in the presence of a suitable coupling agent such as benzotriazole-1-yloxytrispyrrolidinophosphonium hexafluorophosphate (PyBOP®), O-benzotriazol-1-yl-N,N,N',N'-tetramethyluronium hexafluorophosphate (HBTU), O-(7-azabenzotriazol-1-yl)-1,1,3,3-tetramethyluronium hexafluorophosphate (HATU), 1-hydroxybenzotriazole (HOBT), and the like, in the presence of 1-(3-dimethylaminopropyl)-3-ethylcarbodiimide hydrochloride (EDC), 1,3-dicyclohexylcarbodiimide (DCC), and the like, and a base such as N,N-diisopropylethylamine, triethylamine, N-methylmorpholine, and the like. The reaction is typically carried out at 20 to 30° C., preferably at about 25° C., and requires 2 to 4 hours to complete. Suitable reaction solvents are inert organic solvents such as halogenated organic solvents (e.g., methylene chloride, chloroform, and the like), acetonitrile, dimethylformamide, ethereal solvents such as tetrahydrofuran, dioxane, and the like. Preferably, the reaction is carried out with EDC in the presence of a catalytic amount of HOBt in acetonitrile.

Alternatively, this reaction can be carried out by first converting (V) into an active acid derivative such as acid chloride or succinate ester and then reacting it with an amine of formula (IV). The reaction typically requires 2 to 3 hours to complete. The reaction conditions utilized in this reaction depend on the nature of the active acid derivative. For example, if it an acid chloride derivative of (V), the reaction is carried out in the presence of a suitable base (e.g. triethylamine, diisopropylethylamine, pyridine, and the like). Suitable reaction solvents are polar organic solvents such as acetonitrile, N,N-dimethylformamide (DMF), dichloromethane, or any suitable combination thereof.

Compounds of formula (V) can be prepared by methods well known in the art. Some such procedures are described in PCT Application Publication No. WO 00/55144 the disclosure of which is incorporated herein in its entirety. For example a compound of formula (V) where $R^{25}$ and $R^{27}$ are hydrogen, $R^{26}$ is cyclopropylmethylsulfonylmethyl and $R^{28}$ is morpholin-4-yl can be prepared as illustrated and described in Scheme 3 below.

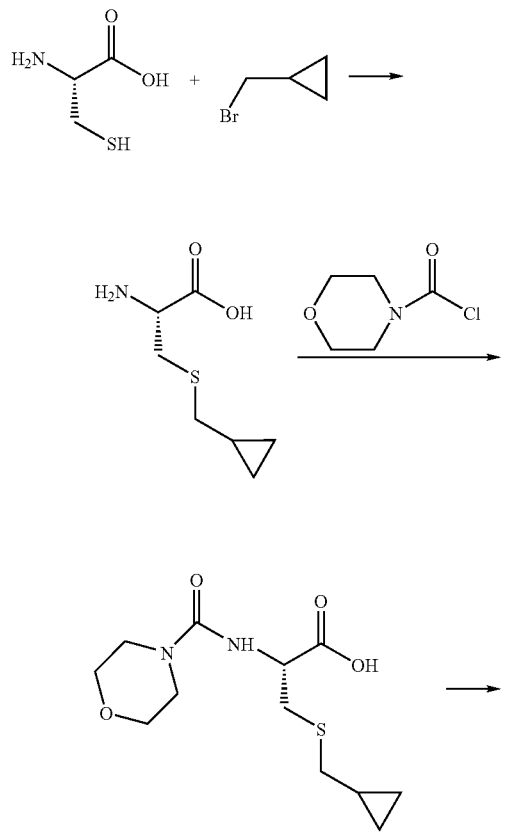

Scheme 3

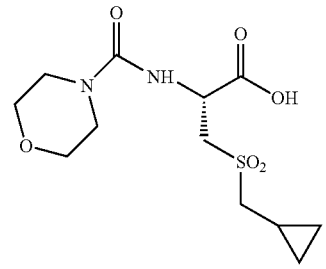

Reaction of cysteine with bromomethylcyclopropane in the presence of an aqueous base such as sodium hydroxide provides 2-amino-2-cyclopropylmethylsulfanylmethylacetic acid. The reaction is carried out in a polar organic solvent such as dioxane or an alcoholic solvent such as methanol, ethanol, and the like. Preferably the reaction is carried out in ethanol.

Treatment of 2-amino-2-cyclopropylmethylacetic acid with morpholin-4-ylcarbonyl chloride in the presence of base such as triethylamine, pyridine, and the like and in a suitable organic solvent such as acetonitrile, and the like provides 2-(morpholin-4-ylcarbonylamino)-2-cyclopropylmethylsulfanyl-methylacetic acid. This reaction can alternatively be carried out by treating 2-amino-2-cyclopropylmethylacetic acid sequentially with N-methyl-N-(trimethylsilyl)trifluoroacetamide and morpholinecarbonyl chloride. This reaction is carried out in halogenated solvent such as dichloromethane, and the like.

Oxidation of 2-(morpholin-4-ylcarbonylamino)-2-cyclopropylmethylsulfanyl-methylacetic acid with an aqueous solution of Oxone® in an alcoholic organic solvent such as methanol, ethanol, and the like, or hydrogen peroxide in acetic acid or hydrogen peroxide and tungstic acid in water then provides the desired compound.

2-(Morpholin-4-ylcarbonylamino)-2-isopropylmethylsulfonylmethylacetic acid can be prepared by following the procedure described above but substituting bromomethyl-cyclo-propane with 3-methylpropyl bromide.

Oxidation of the hydroxy group in (VI) then provides a compound of formula (VII). The reaction is carried out at room temperature. Suitable solvents are halogenated organic solvent such as methylene chloride, chloroform, carbon tetrachloride, and the like. Suitable oxidizing agent are Dess-Martin Periodinane (DMP) (supplier Lancaster), TEMPO/bleach, and the like.

Additional Processes for Preparing Compounds of Formula (VII):

Compounds of formula (VII) can be optionally converted to other compounds of formula (VII) by methods well known in the art. Some such examples are provided below.

Compounds of formula (VII) in which the moiety

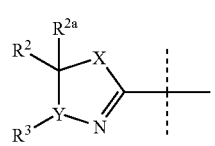

is optionally substituted oxazol-2-yl can be prepared by oxidizing a corresponding compound of formula (VII) in which it is 4,5-dihydrooxazol-2-yl. The oxidation is carried out by first treating (VII) with bromine followed by a base such as 1,8-diazabicyclo[5.4.0]undec-7-ene (DBU) or the like, in a suitable solvent (e.g. dichloromethane, or the like) at 20 to 25° C. and requires 6 to 12 hours to complete.

Compounds of formula (VII) in which $R^{28}$ carries a —C(O)OH can be prepared from a corresponding compound of formula (VII) in which $R^{28}$ carries methoxycarbonyl. The conversion can be effected by treating the methyl ester with sodium hydroxide in a suitable solvent (e.g., ethanol, or the like) at 20 to 25° C. and requires 6 to 12 hours to complete.

Compounds of formula (VII) in which $R^{28}$ carries a —C(O)NR$^{18}$R$^{19}$ can be prepared by reacting a corresponding compound of formula (VII) in which $R^{28}$ carries —C(O)OH with a compound of the formula NHR$^{18}$R$^{19}$. The reaction is carried out in the presence of a suitable coupling agent (PyBOP®, EDC, HBTU, DCC, or the like) and base (e.g., N,N-diisopropylethylamine, triethylamine, or the like) in a suitable solvent (e.g., DMF, or the like) at 20 to 25° C. and requires 2 to 4 hours to complete.

Compounds of formula (VII) in which $R^{26}$ contains a sulfonyl moiety can be prepared by oxidizing a corresponding compound of formula (VII) containing a sulfanyl moiety. The oxidation is carried out with a suitable oxidizing agent (e.g. potassium peroxymonosulfate (OXONE®, or the like) in a suitable solvent (e.g. methanol, water, or the like, or any suitable combination thereof) at ambient temperature and requires 16 to 24 hours to complete.

A compound of formula (VII) in which the moiety

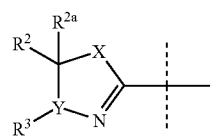

is 1,1-dioxo-1H-1λ$^6$-benzo[b]thien-2-yl can be prepared by oxidizing a corresponding compound of formula (VII)) in which it is benzo[b]thien-2-yl.

A compound of formula (VII) can be prepared as a pharmaceutically acceptable acid addition salt by reacting the free base form of the compound with a pharmaceutically acceptable inorganic or organic acid. Alternatively, a pharmaceutically acceptable base addition salt of a compound of formula (VII) can be prepared by reacting the free acid form of the compound with a pharmaceutically acceptable inorganic or organic base. Inorganic and organic acids and bases suitable for the preparation of the pharmaceutically acceptable salts of compounds of formula (VII) are set forth in the definitions section of this application. Alternatively, the salt forms of the compounds of formula (I) can be prepared using salts of the starting materials or intermediates.

The free acid or free base forms of the compounds of formula (VII) can be prepared from the corresponding base addition salt or acid addition salt form. For example, a compound of formula (VII) in an acid addition salt form can be converted to the corresponding free base by treating with a suitable base (e.g. ammonium hydroxide solution, sodium hydroxide, or the like). A compound of formula (VII) in a base addition salt form can be converted to the corresponding free acid by treating with a suitable acid (e.g. hydrochloric acid, etc).

The N-oxides of compounds of formula (VII) can be prepared by methods known to those of ordinary skill in the art. For example, N-oxides can be prepared by treating an unoxidized form of the compound of formula (VII) with an oxidizing agent (e.g. trifluoroperacetic acid, permaleic acid, perbenzoic acid, peracetic acid, meta-chloroperoxybenzoic acid, or the like) in a suitable inert organic solvent (e.g. a halogenated hydrocarbon such as dichloromethane) at approximately 0° C. Alternatively, the N-oxides of the compounds of formula (VII) can be prepared from the N-oxide of an appropriate starting material.

Compounds of formula (VII) in unoxidized form can be prepared from N-oxides of compounds of formula (VII) by treating with a reducing agent (e.g. sulfur, sulfur dioxide, triphenyl phosphine, lithium borohydride, sodium borohydride, phosphorus trichloride, tribromide, or the like) in an suitable inert organic solvent (e.g. acetonitrile, ethanol, aqueous dioxane, or the like) at 0 to 80° C.

Prodrug derivatives of the compounds of formula (VII) can be prepared by methods known to those of ordinary skill in the art (e.g. for further details see Saulnier et al. (1994), *Bioorganic and Medicinal Chemistry Letters*. 4:1985). For example, appropriate prodrugs can be prepared by converting an acid group in a compound of formula (VII) to an ester group.

Protected derivatives of the compounds of formula (VII) can be made by means known to those of ordinary skill in the art. A detailed description of the techniques applicable to the creation of protecting groups and their removal can be found in T. W. Greene, *Protecting Groups in Organic Synthesis*, John Wiley & Sons, Inc. 1981.

SYNTHETIC EXAMPLES

The following preparations and examples are given to enable those skilled in the art to more clearly understand and to practice the present invention. They should not be considered as limiting the scope of the invention, but merely as being illustrative and representative thereof.

Example 1

Synthesis of (S)-2-amino-1-benzoxazol-2-yl-propan-1-ol hydrochloride

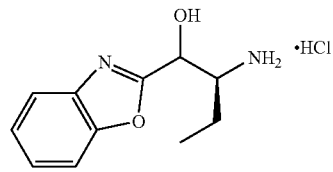

Step 1

To a solution of benzoxazole (28.6 g, 240 mmol) in toluene (150 mL) was added during ca 20 min., at ca –4° C. a 2M solution of isopropyl-magnesium chloride in THF (120 mL, 240 mmol). The red-brown mixture was stored at ca –4° C. and used as needed.

Step 2

To a solution of (S)-2-Boc-aminobutanol (50 g; 264 mmol) in dichloromethane (500 mL) and water (350 mL) were added at 20° C. TEMPO (0.01 eq), sodium bromide (1 eq) and sodium hydrogencarbonate (3 eq). The reaction mixture was stirred at 0° C. and diluted bleach (1.3 eq, 450 mL) was added over 40 min. The reaction mixture was stirred for 30 min. at 0° C. and then quenched with aq. thiosulfate. After decantation and extractions (dichloromethane), the organic phase was washed with brine, dried and concentrated in vacuo to dryness, giving (S)-2-(tert-butoxycarbonyl)-amino-butyraldehyde as a low-melting solid (38.1 g; yield: 77%). $C_9H_{17}NO_3$; MW=187.2; $T_{melt}$=44° C.; NMR (CDCl$_3$, ppm): 0.97 (t, J=7 Hz, 3H), 1.45 (s, 9H), 1.68 (m, 1H), 1.91 (m, 1H), 4.20 (lq, J=6.5 Hz, 1H), 5.09 (1s, 1H (mobile)) and 9.59 (s, 1H); SM (EI; m/z): 158 (M$^+$—CHO), 102, 57.

Step 3

A solution of (S)-2-(tert-butoxycarbonyl)amino-butyraldehyde (30 g; 160 mmol) in toluene (150 mL) was added over 30 min. at −5° C. to a solution of Grignard reagent of benzoxazole (prepared as described in Step 1 above). The reaction mixture was stirred for 0.5 h at 0° C., then 2.5 h at RT. Quenching with 5% aq. acetic acid, washings with 5% aq. sodium carbonate, then brine and concentration to dryness gave crude (S)-2-(tert-butoxycarbonyl)-amino-1-benzoxazol-2-yl-propan-1-ol. The residue was diluted with toluene, and silica gel was added. The slurry was filtered. Elution by toluene removed the non-polar impurities. Then an 8/2 mixture of toluene and ethyl acetate desorbed the (S)-2-(tert-butoxycarbonyl) amino-1-benzoxazol-2-yl-propan-1-ol. Concentration to dryness gave a red resin (37 g ; yield=75% ; 7/3 mixture of diastereomers). $C_{16}H_{22}N_2O_4$; MW=306.4 ; NMR (DMSO, ppm): 0.86 (t, J=7.5 Hz, 3H), 1.14 (s, 2.7H), 1.27 (s, 6.3H), 1.40 (m, 1H), 1.56 (m, 0.7H), 1.79 (m, 0.3H), 3.75 (m, 1H), 4.60 (dd, J=8 and 5.5 Hz, 0.3H), 4.84 (t, J=5.5 Hz, 0.7H), 5.94 (d, J=5.5 Hz, 0.7H (mobile)), 6.14 (d, J=5.5 Hz, 0.3H (mobile)), 6.54 (d, J=9.5 Hz, 0.7H (mobile)), 6.71 (d, J=9.5 Hz, 0.3H (mobile)), 7.35 (m, 2H) and 7.69 (m, 2H); SM (ESP; m/z): 307 (MH$^+$).

Step 3

To a solution of (S)-2-(tert-butoxycarbonyl)amino-1-benzoxazol-2-yl-propan-1-ol (26.3 g; 86 mmol) in isopropanol (118 mL) at 20–25° C. was added trimethylchlorosilane (1.4 eq). The solution was stirred for 5 h at 50° C. Concentration of the reaction mixture to 52 mL followed by addition of isopropyl ether (210 mL), filtration and drying under vacuum afforded (S)-2-amino-1-benzoxazol-2-yl-propan-1-ol hydrochloride salt as a grey solid (16.4 g; yield=79%; mixture of diastereomers). $C_{11}H_{15}ClN_2O_2$; MW=242.7; $T_{melt}$=138° C.; NMR (DMSO, ppm): 0.91 (t, J=7 Hz, 0.9H), 0.93 (t, J=7 Hz, 2.1H), 1.66 (m, 2H), 3.54 (m, 1H), 5.02 (t, J=5 Hz, 0.7 H), 5.24 (m, 0.3 H), 6.89 (m, 0.3H (mobile)), 7.06 (d, J=5.5 Hz, 0.7H (mobile)), 7.42 (m, 2H), 7.77 (m, 2H), 8.24 (m, 2.1H) and 8.35 (m, 0.9H); SM (ESP; m/z): 207 (MH$^+$), 150, 132.

Example 2

Synthesis of (S)-2-(tert-butoxycarbonyl)amino-1-(oxazolo[4,5-b]pyridin-2-yl)propan-1-ol

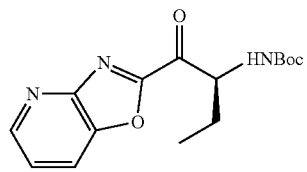

Step 1

A mixture of 2-amino-3-hydroxypyridine (11 g, 100 mmol), triethylorthoformate (80 ml) and p-toluenesulfonic acid (61 mg) was heated at 140° C. for 8 hours. Excess triethylorthoformate was removed under vacuum and oxazolo[4,5-b]pyridine was crystalized from ethyl acetate (9 g).

Step 2

In a clean roundbottom flask equipped with stir bar was placed oxazolo[4,5-b]pyridine (600 mg, 5 mmol) in 30 mL THF and the reaction mixture was cooled to 0° C. under N$_2$ atmosphere. Isopropylmagnesium chloride (2M in THF, 2.5 ml, 5 mmol ) was added. After stirring for 1 h at 0° C., (S)-2-(tert-butoxycarbonyl)aminobutyraldehyde (573 mg, 3 mmol) in 20 ml THF was added. The ice bath was removed and the reaction mixture was allowed to warm to room temperature. After 2 h, the reaction mixture was quenched with saturated ammonium chloride solution and concentrated to dryness. The residue was extracted with EtOAc, then washed with brine, dried with anhyd. MgSO$_4$, filtered and concentrated. The crude product was purified by chromatograph to yield 383 mg of the desired compound.

H$^1$ NMR (DMSO-d$_6$): 8.42(1H, m), 8.18(1H, m), 7.3(1H, m), 6.8, 6.6(1H, dd, d, OH, diastereomer), 6.3, 6.02(1H, d, d, NH, diastereomer), 4.82, 4.5(1H, m,m, diastereomer), 1.8–1.3(2H, m), 1.2, 1.05(9H, s,s, diastereomer), 0.89(3H, m). MS: 306.2(M−1), 308.6(M+1).

Example 3

Synthesis of N-[1-(R)-(1S-benzoxazol-2-ylcarbonyl-propylcarbamoyl)-2-cyclopropylmethylsulfonyl-ethyl]morpholine-4-carboxamide

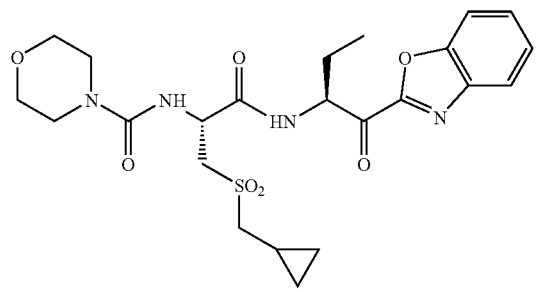

Step 1

L-Cysteine (100 g, 0.825 mol) was suspended in ethanol (850 mL). A solution of sodium hydroxide (1.65 mol) in ethanol (650 mL) was added during 40 min at 20–25° C. To the solution was added bromomethylcyclopropane (0.907 mol) at 25–30° C. The reaction mixture was stirred at ambient temperature overnight, the neutralized with 2N HCl (300 mL). The suspension was concentrated under vacuum to 400 mL, then water (750 mL) was added, and pH was adjusted to 6.5 with 2N HCl. The mixture was stirred for 2 h at 0–5° C., the precipitate was filtered, washed with water and dried under vacuum to give (R)-2-amino-3-cyclopropylmethylsulfanylpropionic acid as a white crystalline solid (128.2 g; yield=88.6 %). $C_7H_{13}NO_2S$; MW=175.3; $T_{melt}$=2090 C; NMR (DMSO, ppm): 0.20 (m, 2H), 0.50 (m, 2H), 0.94 (m, 1H), 2.50 (m, 2H), 2.78 (dd, J=14.5 and 8.5 Hz, 1 H), 3.08 (dd, J=14.5 and 4 Hz, 1 H) and 7.64 (ls, 1H (mobile)); SM (EI; m/z): 130 (M$^+$—COOH), 89, 74.

Step 2

(R)-2-Amino-3-cyclopropyl-methylsulfanylpropionic acid (100 g; 0.570 mol) and triethylamine (1.25 mol) were suspended in acetonitrile (1500 mL) and water (150 mL). Morpholinecarbonyl chloride (0.656 mol) was added for 4 h at 20–25° C. The solution was stirred at room temperature overnight, then concentrated under vacuum to 400 mL. Water (250 mL) was added to the suspension, and pH was adjusted to 12.5 with 2N sodium hydroxide (ca 1.20 mol). The aqueous phase was washed with dichloromethane, then dichloromethane was added and pH was adjusted to 2.0–2.5 with 2N HCl (ca 0.57 mol). The dichloromethane phase was washed with water and concentrated to ca 400 mL. Dichloromethane was replaced by 2-propanol by distillation under vacuum at constant volume. Water (500 mL), tungstic acid (11.4 mmol) and 30% hydrogen peroxide (1.25 mol) were added at 20–30° C. The reaction mixture was stirred vigorously for 5 h at 30° C., and then at room temperature overnight. Excess peroxide was reduced with aqueous sodium metabisulfite. The product was extracted with a mixture of ethyl acetate and 2-propanol. Concentration under vacuum, trituration in ethyl acetate, filtration and drying overnight under vacuum afforded (R)-3-cyclopropylmethylsulfonyl-2-(morpholine-4-carbonylamino)-propionic acid as a white crystalline solid (145.5 g; yield=80%). $C_{12}H_{20}N_2O_6S$; MW=320.4; $T_{melt}$=136° C.; NMR (DMSO, ppm): 0.35 (m, 2H), 0.60 (m, 2H), 1.03 (m, 1H), 3.02 (dd, J=14.5 and 7.5 Hz, 1H), 3.09 (dd, J=14.5 and 7 Hz, 1H), 3.27 (m, 4H), 3.54 (m, 6H), 4.51 (ddd, J 8.5, 8 and 3.5 Hz, 1H), 7.11 (d, J=8 Hz, 1H (mobile)) and 12.79 (ls, 1H (mobile)); SM (ESP; m/z): 321 (MH$^+$).

Step 3

Triethylamine (144 mmol) was added at room temperature to a suspension of (R)-3-cyclopropylmethanesulfonyl-2-(morpholine-4-carbonylamino)-propionic acid (46.2 g; 144 mmol) and (S)-2-amino-1-benzoxazol-2-yl-propan-1-ol. HCl salt (35 g; 144 mmol) in dichloromethane (350 mL). A fresh solution of EDC.HCl (202 mmol), HOBT (37 mmol) and dichloromethane (350 mL) was added during ca 2 h at 0–5° C. The mixture was neutralized with aqueous 5% sodium hydrogencarbonate (104 mmol). After decantation, the organic phase was washed with aqeous 5% acetic acid, aqueous 5% sodium hydrogencarbonate, then water. TEMPO (1.4 mmol), sodium bromide (144 mmol) and sodium hydrogencarbonate (144 mmol) were added at 0° C. A solution of sodium hypochlorite (187 mmol) in water (400 ml) was added under vigorous stirring during ca 2 h at 0–5° C. The mixture was stirred for 3–4 h at 0–5° C., then quenched with aqueous 10% sodium thiosulfate (130 mmol). After decantation, the organic phase was washed with water and dried over sodium sulfate. The solution was concentrated to ca 800 mL, and dichloromethane was replaced by ethanol by distillation at constant volume at ca 40° C. N-[1-(R)-(1S-benzoxazol-2-yl-carbonylpropyl-carbamoyl)-2-cyclopropylmethylsulfonylethyl]morpholine-4-carboxamide (ethanol solvate) crystallised out and was filtered off, washed with ethanol and dried under vacuum (49.7 g; yield=68%; white crystalline solid). $C_{23}H_{30}N_4O_7S$; MW=506.6; $T_{melt}$=89° C.; NMR (DMSO, ppm): 0.34 (m, 2H), 0.57 (m, 2H), 0.97 (t, J=7.5 Hz, 3H), 1.03 (m, 1H), 1.77 (m, 1H), 2.01 (m, 1H), 3.01 (dd, J=14.5 and 7.5 Hz, 1H), 3.12 (dd, J=14.5 and 7 Hz, 1H), 3.29 (m, 4H), 3.47 (m, 2H), 3.53 (m, 4H), 4.69 (dt, J=8.5 and 5 Hz, 1H), 5.20 (ddd, J=8.5, 6.5 and 4.5 Hz, 1H), 6.98 (d, J=8.5 Hz, 1H (mobile)), 7.55 (lt, J=8.5 Hz, 1H), 7.65 (lt, J=8.5 Hz, 1H), 7.90 (ld, J=8.5 Hz, 1H), 8.00 (ld, J=8.5 Hz, 1H) and 8.63 (d, J=6.5 Hz, 1H (mobile)); SM (ESP; m/z): 507 (MH$^+$), 466, 303.

Proceeding as described above but substituting bromomethylcyclopropane with 1-bromo-2-methylpropane gave N-[1-(R)-(1S-benzoxazol-2-ylcarbonylpropyl-carbamoyl)-2-(2-methylpropylsulfonylethyl]morpholine-4-carboxamide. $C_{23}H_{32}N_4O_7S$; MW=508.6 ; $T_{melt}$=111° C. ; NMR (DMSO, ppm): 0.97 (t, J=7 Hz, 3H), 1.01 (2d, J=7 Hz, 6H), 1.76 (m, 1H), 2.02 (m, 1H), 2.18 (m, 1H), 2.99 (dd, J=14 and 7 Hz, 1H), 3.04 (dd, J=14 and 6.5 Hz, 1H), 3.29 (m, 4H), 3.44 (m, 2H), 3.54 (m, 4H), 4.70 (dt, J=8.5 and 4 Hz, 1H), 5.19 (ddd, J=8.5, 6.5 and 4.5 Hz, 1H), 6.96 (d, J=8.5 Hz, 1H (mobile)), 7.55 (lt, J=8.5 Hz, 1H), 7.64 (lt, J=8.5 Hz, 1H), 7.89 (ld, J=8.5 Hz, 1H), 8.00 (ld, J=8.5 Hz, 1H) and 8.69 (d, J=6.5 Hz, 1H (mobile)); SM (ESP; m/z): 509 (MH$^+$), 305.

In step 2 above, (R)-3-(3-methylpropylsulfonyl)-2-(morpholine-4-carbonylamino]-propionic acid was crystallized from ethyl acetate in 82% yield. $C_{12}H_{22}N_2O_6S$; MW=322.4; $T_{melt}$=124° C.; NMR (DMSO, ppm): 1.02 (t, J=6.5 Hz, 6H), 2.18 (m, 1H), 2.98 (dd, J=14.5 and 7 Hz, 1H), 3.04 (dd, J=14.5 and 6.5 Hz, 1H), 3.28 (m, 4H), 3.45 (dd, J=15 and 3.5 Hz, 1H), 3.54 (m, 4H), 3.57 (dd, J=15 and 9.5 Hz, 1H), 4.50 (ddd, J=9.5, 8 and 3.5 Hz, 1H), 7.09 (d, J=8 Hz, 1H (mobile)) and 12.43 (ls, 1H (mobile)); SM (ESP; m/z): 323 (MH$^+$).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:

1. A process of preparing a reagent of formula (Ia):

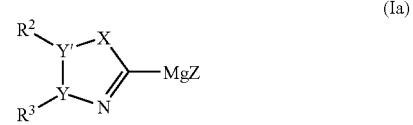

(Ia)

comprising reacting a compound of formula (I):

(I)

wherein:

X is —O— or —S—;

Y is nitrogen or —CR$^{3a}$—;

Y' is nitrogen or —CR$^{2a}$— provided that Y and Y' are not simultaneously nitrogen;

one of $R^2$ and $R^3$ is hydrogen, $(C_{1-6})$alkyl, $(C_{1-6})$alkoxy, $(C_{1-6})$alkoxy$(C_{1-6})$alkyl, $(C_{1-6})$alkylthio, $(C_{5-6})$cycloalkyl, $(C_{5-6})$cycloalkylalkyl, halo, nitro, halo$(C_{1-3})$alkyl, $(C_{6-12})$aryl, heteroaryl, heterocycloalkyl, $(C_{6-12})$aryl$(C_{1-6})$alkyl, heteroaryl$(C_{1-6})$alkyl, $(C_{1-6})$alkylsulfonyl, $(C_{6-12})$arylsulfonyl, $(C_{6-12})$aryl$(C_{1-6})$alkylsulfonyl, heteroarylsulfonyl, heteroaryl$(C_{1-6})$alkylsulfonyl, aminosulfonyl, $(C_{1-6})$alkylaminosulfonyl, $(C_{1-6})$dialkylaminosulfonyl, —CONR$^4$R$^5$ (where $R^4$ and $R^5$ are independently of each other hydrogen, $(C_{1-6})$alkyl, $(C_{1-6})$alkoxy, aryl, aryl$(C_{1-6})$alkyl, heteroaryl, heteroaryl$(C_{1-6})$alkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or $R^4$ and $R^5$ together with the nitrogen atom to which they are attached form heterocycloamino), —NHCOR$^6$ (where $R^6$ is $(C_{1-6})$alkyl, $(C_{6-12})$aryl, aryl$(C_{1-6})$alkyl, heteroaryl, heteroaryl$(C_{1-6})$alkyl, $(C_{5-6})$cycloalkyl, $(C_{5-6})$cycloalkyl$(C_{1-6})$alkyl, heterocycloalkyl, or heterocycloalkyl$(C_{1-6})$alkyl), —SO$_2$NR$^7$R$^8$ (where $R^7$ and $R^8$ are independently of each other hydrogen, $(C_{1-6})$alkyl, $(C_{6-12})$aryl, $(C_{6-12})$aryl$(C_{1-6})$alkyl, heteroaryl, heteroarylalkyl, $(C_{5-6})$cycloalkyl, $(C_{5-6})$cycloalkyl$(C_{1-6})$alkyl, heterocycloalkyl, or heterocycloalkyl$(C_{1-6})$alkyl, or $R^7$ and $R^8$ together with the nitrogen atom to which they are attached form heterocycloamino), -alkylene-CONR$^4$R$^5$ (where $R^4$ and $R^5$ are as defined above), —alkylene-NHCOR$^6$ (where $R^6$ is as defined above), or -alkylene-SO$_2$NR$^7$R$^8$ (where $R^7$ and $R^8$ are as defined above); and the other of $R^2$ and $R^3$ is hydrogen or $(C_{1-6})$alkyl wherein within $R^2$ or $R^3$ said aryl, heteroaryl, or heterocycloalkyl is optionally substituted further with one, two, or three substituents independently selected from the group consisting of $(C_{1-6})$alkoxy, $(C_{1-6})$alkyl, $(C_{6-12})$aryl$(C_{1-6})$alkyl, halo, nitro, and halo$(C_{1-3})$alkyl; or when Y and Y' are carbon, then $R^2$ and $R^3$ together with the atoms to which they are attached form an optionally substituted benzene, napthyl, $(C_{3-6})$cycloalkyl, or an aromatic or non-aromatic heterocyclic ring;

$R^{2a}$ and $R^{3a}$ are independently hydrogen or alkyl; or $R^{2a}$ and $R^{3a}$ together form a covalent bond, provided that when Y or Y' is nitrogen, $R^{2a}$ and $R^3$ or $R^2$ and $R^{3a}$ together form a covalent bond; with a Grignard reagent wherein Z is a halogen provided that (I) is not 1,2,4- or 1,3,4-oxadiazole.

2. The process of claim 1 wherein $R^2$ and $R^3$ together with the atoms to which they are attached form an optionally substituted benzene.

3. The process of claim 1 wherein the compound of formula (I) is benzoxazole, benzothiazole, 5-phenylbenzoxazole, 5, or 6-methoxybenzoxazole, 5-trifluorobenzoxazole, 5-nitrobenzoxazole, 5-chloro-benzoxazole, oxazolo-[4,5-b]pyridine or 5-aminosulfonylbenzoxazole.

4. The process of claim 1 wherein the Grignard reagent is selected from the group consisting of n-butylmagnesium chloride, isopropylmagnesium chloride, phenylmagnesium chloride, n-butylmagnesium bromide, isopropylmagnesium bromide, or phenylmagnesium bromide and the reaction is carried out in an ethereal organic solvent or a mixture of ethereal and an aromatic organic solvent from about −10° to about 10° C.

5. The process of claim 1 which further comprises reacting the nucleophilic heteroaryl or unsaturated heterocycloalkylmagnesium reagent with an aldehyde of formula (II):

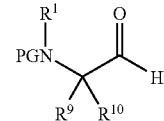

(II)

where:

PG is an amino protecting group;

$R^1$ is hydrogen or alkyl, or $R^1$ together with $R^{10}$ and the atoms to which they are attached form heterocycloamino;

R9 is hydrogen or (C1-6)alkyl; and $R^{10}$ is:

(i) $(C_{1-6})$alkyl optionally substituted with halo, nitro, —SR$^{11}$, —C(O)NR$^{11}$R$^{11}$, —P(O)(OR$^{11}$)OR$^{11}$, —OP(O)(OR$^{11}$)OR$^{11}$, —S(O)R$^{12}$, or —S(O)$_2$R$^{12}$ wherein R$^{11}$ at each occurrence independently is hydrogen, $(C_{1-6})$alkyl or halo-substituted $(C_{1-3})$alkyl and $R^{12}$ is alkyl or halo-substituted alkyl; or (ii) $(C_{5-6})$cycloalkyl$(C_{2-3})$alkyl, hetero$(C_{3-6})$cycloalkyl$(C_{2-3})$alkyl, $(C_{6-12})$aryl$(C_{2-3})$alkyl or hetero$(C_{5-6})$aryl$(C_{2-3})$alkyl, wherein said cycloalkyl, heterocycloalkyl, aryl or heteroaryl optionally is substituted further with 1 to 5 radicals independently selected from the group consisting of alkyl, alkylidene, halo, halo-substituted $(C_{1-4})$alkyl, nitro, —X$^1$NR$^{14}$C(O)OR$^{14}$, —X$^1$NR$^{14}$C(O)NR$^{14}$R$^{14}$, —X$^1$NR$^{14}$C(NR$^{14}$)NR$^{14}$R$^{14}$, —X$^1$OR$^{14}$, —X$^1$SR$^{14}$, —X$^1$C(O)NR$^{14}$R$^{14}$, —X$^1$S(O)$_2$NR$^{14}$R$^{14}$, —X$^1$P(O)(OR$^{14}$)OR$^{14}$, —X$^1$OP(O)(OR$^{14}$)OR$^{14}$, —X$^1$NR$^{14}$C(O)R$^{15}$, —X$^1$S(O)R$^{15}$, and —X$^1$S(O)$_2$R$^{15}$ wherein X$^1$ is a bond or $(C_{1-6})$alkyl, R$^{14}$ at each occurrence independently is hydrogen, $(C_{1-6})$alkyl or halo-substituted $(C_{1-3})$alkyl, and R$^{15}$ is $(C_{1-6})$alkyl, halo-substituted $(C_{1-3})$alkyl, or halo; or (iii) $R^9$ and $R^{10}$ taken together with the carbon atom to which both R$^9$ and R$^{10}$ are attached form $(C_{3-8})$cycloalkylene or heterocycloalkylene, wherein said cycloalkylene or heterocycloalkylene is optionally substituted with 1 to 3 radicals independently selected from the group consisting of $(C_{1-6})$alkyl, $(C_{1-6})$alkylidene, halo, halo-substituted $(C_{1-4})$alkyl, nitro, —X$^2$NR$^{14}$C(O)OR$^{14}$, —X$^2$NR$^{14}$C(O)NR$^{14}$R$^{14}$, —X$^2$NR$^{14}$C(NR$^{14}$)NR$^{14}$R$^{14}$, —X$^2$OR$^{14}$, —X$^2$SR$^{14}$, —X$^2$C(O)NR$^{14}$R$^{14}$, —X$^2$S(O)$_2$NR$^{14}$R$^{14}$, —X$^2$P(O)(OR$^{14}$)OR$^{14}$, —X$^2$OP(O)(OR$^{14}$)OR$^{14}$, —X$^2$NR$^{14}$C(O)R$^{15}$, —X$^2$S(O)R$^{15}$ and —X$^2$S(O)$_2$R$^{15}$ wherein X$^2$ is a bond or $(C_{1-6})$alkylene, R$^{14}$ at each occurrence independently is hydrogen, $(C_{1-6})$alkyl or halo-substituted $C_{1-3}$alkyl, and R$^{15}$ is $(C_{1-6})$alkyl, halo-substituted $(C_{1-3})$alkyl, or halo; to provide a compound of formula (III):

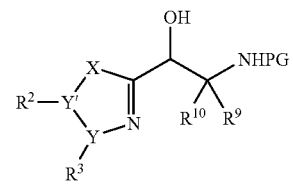

(III)

where:
X, Y, Y', PG, R², R²ᵃ, R³, R⁹, and R¹⁰ are as defined above;
(i) optionally removing the amino protecting group;
(ii) optionally converting the compound obtained in step (i) above, to an acid addition salt;
(iii) optionally converting a salt form of a compound of formula (III) to a free base;
(iv) optionally separating individual isomers;
(v) optionally modifying any of the X, R², R³, R⁹ and R¹⁰ groups.

6. The process of claim 5 which further comprises removing the amino protecting group in compound (III) to provide a compound of formula (IV):

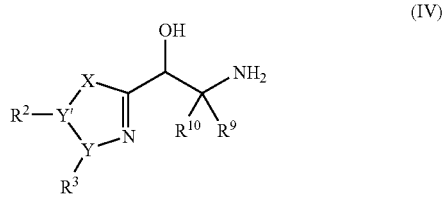

(IV)

where Y, X, R², R³, R⁹ and R¹⁰ are as defined above; and optionally forming an acid addition salt and reacting (IV) with a compound of formula (V):

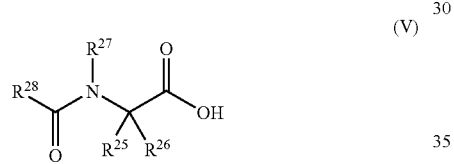

(V)

where:
R²⁵ and R²⁷ are independently of each other hydrogen or (C₁₋₆)alkyl;
R²⁸ is:
(i) (C₁₋₆)alkyl optionally substituted by cyano, halo, nitro, —NR¹⁴R¹⁴, —NR¹⁴C(O)OR¹⁴, —NR¹⁴C(O)NR¹⁴R¹⁴, —NR¹⁴C(NR¹⁴)NR¹⁴R¹⁴, —OR¹⁴, —SR¹⁴, —C(O)NR¹⁴R¹⁴, —S(O)₂NR¹⁴R¹⁴, —P(O)(OR¹⁴)OR¹⁴, —OP(O)(OR¹⁴)OR¹⁴, —NR¹⁴C(O)R¹⁵, —S(O)R¹⁵, —S(O)₂R¹⁵, —C(O)R¹⁵, —OR¹⁶, —SR¹⁶, —S(O)R¹⁶, —S(O)₂R¹⁶, —C(O)NR¹⁶R¹⁷, —NR¹⁶R¹⁷, —NR¹⁷C(O)R¹⁶, —NR¹⁷C(O)OR¹⁶, —NR¹⁷C(O)NR¹⁶R¹⁷ or —NR¹⁷C(NR¹⁷)NR¹⁶R¹⁷, wherein R¹⁴ and R¹⁵ are as defined above, R¹⁶ is (C₃₋₁₂)cycloalkyl(C₀₋₆)alkyl, heterocycloalkyl(C₀₋₆)alkyl, (C₆₋₁₂)aryl(C₀₋₆)alkyl, heteroaryl(C₀₋₆)alkyl, (C₉₋₁₂)bicycloaryl(C₀₋₆)alkyl or heterobicycloaryl(C₀₋₆)alkyl and R¹⁷ at each occurrence independently is hydrogen or (C₁₋₆)alkyl; or
(ii) (C₃₋₆)cycloalkyl(C₀₋₆)alkyl, hetero(C₃₋₁₂)cycloalkyl (C₀₋₆)alkyl, (C₆₋₁₂)aryl(C₀₋₆)alkyl, hetero(C₅₋₁₂)aryl (C₀₋₆)alkyl, (C₉₋₁₂)bicycloaryl(C₀₋₆)alkyl or hetero(C₈₋₁₂)bicycloaryl(C₀₋₆)alkyl; or
(iii) (C₃₋₆)cycloalkyl(C₀₋₆)alkyl, hetero(C₃₋₆)cycloalkyl (C₀₋₆)alkyl, phenyl(C₀₋₆)alkyl or hetero(C₅₋₆)aryl(C₀₋₆) alkyl, wherein said cycloalkyl, heterocycloalkyl, phenyl or heteroaryl is substituted by —R¹⁸, —X³OR¹⁸, —X³SR¹⁸, —X³S(O)R¹⁸, —X³S(O)₂R¹⁸, —X³C(O)R¹⁸, —X³C(O)OR¹⁸, —X³C(O)NR¹⁸R¹⁹, —X³NR¹⁸R¹⁹, —X³NR¹⁹C(O)R¹⁸, —X³NR¹⁹C(O)OR¹⁸, —X³NR¹⁹C(O)NR¹⁸R¹⁹ or —X³NR¹⁹C(NR¹⁹) NR¹⁸R¹⁹, wherein X³ is a bond or (C₁₋₆)alkylene, R¹⁸ is (C₃₋₆)cycloalkyl(C₀₋₆)alkyl, hetero(C₃₋₆)cycloalkyl (C₀₋₆)alkyl, phenyl(C₀₋₆)alkyl or hetero(C₅₋₆)aryl(C₀₋₆) alkyl and R¹⁹ at each occurrence independently is hydrogen or (C₁₋₆)alkyl;

wherein within R²⁸ any alicyclic or aromatic ring system present may be substituted further by 1 to 5 radicals independently selected from the group consisting of (C₁₋₆)alkyl, (C₁₋₆)alkylidene, cyano, halo, halo-substituted (C₁₋₄)alkyl, nitro, —X⁴NR¹⁴R¹⁴, —X⁴NR¹⁴C(O) OR¹⁴, —X⁴NR¹⁴C(O)NR¹⁴R¹⁴, —X⁴NR¹⁴C(NR¹⁴) NR¹⁴R¹⁴, —X⁴OR¹⁴, —X⁴SR¹⁴, —X⁴C(O)OR¹⁴, —X⁴C(O)NR¹⁴R¹⁴, —X⁴S(O)₂NR¹⁴R¹⁴, —X⁴P(O) (OR¹⁴)OR¹⁴, —X⁴OP(O)(OR¹⁴)OR¹⁴, —X⁴NR¹⁴C (O)R¹⁵, —X⁴S(O)R¹⁵, —X⁴S(O)₂R¹⁵ and —X⁴C(O) R¹⁵, wherein X⁴ is a bond or (C₁₋₆)alkylene, R¹⁴ and R¹⁵ are as defined above; and R²⁶ is:
(i) (C₁₋₆)alkyl optionally substituted with cyano, aryl, halo, nitro, —NR¹⁴R¹⁴, —NR¹⁴C(O)OR¹⁴, —NR¹⁴C (O)NR¹⁴R¹⁴, —NR¹⁴C(NR¹⁴)NR¹⁴R¹⁴, —OR¹⁴, —SR¹⁴, —C(O)NR¹⁴R¹⁴, —S(O)₂NR¹⁴R¹⁴, —P(O) (OR¹⁴)OR¹⁴, —OP(O)(OR¹⁴)OR¹⁴, —NR¹⁴C(O)R¹⁵, —NR¹⁴SO₂R¹⁵, —S(O)R¹⁵, —S(O)₂R¹⁵, —C(O)R¹⁵, —OR¹⁶, —SR¹⁶, —S(O)R¹⁶, —S(O)₂R¹⁶, —OC(O) R¹⁶, —NR¹⁶R¹⁷, —NR¹⁷C(O)R¹⁶, —NR¹⁷C(O) OR¹⁶, —C(O)NR¹⁶R¹⁷, —S(O)₂NR¹⁶R¹⁷, —NR¹⁷C(O) NR¹⁶R¹⁷ or —NR¹⁷C(NR¹⁷)NR¹⁶R¹⁷, wherein R¹⁴, R¹⁵, R¹⁶ and R¹⁷ are as defined above, and wherein within R¹⁶ said cycloalkyl, heterocycloalkyl, aryl, heteroaryl, bicycloaryl or heterbicycloaryl ring optionally is substituted by a group selected from —R²⁰, —X⁵OR²⁰, —X⁵SR²⁰, —X⁵S(O)R²⁰, —X⁵S(O)₂R²⁰, —X⁵C(O)R²⁰, —X⁵C(O)OR²⁰, —X⁵OC(O)R²⁰, —X⁵NR²⁰R²¹, —X⁵NR²¹C(O)R²⁰, —X⁵NR²¹C(O) OR²⁰, —X⁵C(O)NR²⁰R²¹, —X⁵S(O)₂NR²⁰R²¹, —X⁵NR¹⁹C(O)NR²⁰R²¹ and —X⁵NR²¹C(NR²¹) NR²⁰R²¹, wherein X⁵ is a bond or (C₁₋₆)alkylene, R²⁰ is hydrogen or (C₁₋₆)alkyl and R²¹ is (C₃₋₁₂)cycloalkyl (C₀₋₆)alkyl, hetero(C₃₋₁₂)cycloalkyl-(C₀₋₆)alkyl, (C₆₋₁₂)aryl(C₀₋₆)alkyl, hetero(C₅₋₁₂)aryl(C₀₋₆)alkyl, (C₉₋₁₂)polycycloaryl(C₀₋₆)alkyl or hetero(C₈₋₁₂)polycycloaryl(C₀₋₆)alkyl; or
(ii) a group selected from (C₃₋₁₂)cycloalkyl(C₀₋₆)alkyl, hetero(C₃₋₁₂)cycloalkyl(C₀₋₆)alkyl, (C₆₋₁₂)aryl(C₀₋₆) alkyl, hetero(C₅₋₁₂)aryl(C₀₋₆)alkyl, (C₉₋₁₂)polycycloaryl(C₀₋₆)alkyl and hetero(C₈₋₁₂)polycycloaryl(C₀₋₆)alkyl, wherein said cycloalkyl, heterocycloalkyl, aryl, heteroaryl, polycycloaryl or heterpolycycloaryl ring optionally is substituted by a group selected from —R²⁰, —X⁶R²⁰, —X⁶SR²⁰, —X⁶S(O)R²⁰, —X⁶S(O)₂R²⁰, —X⁶C(O) R²⁰, —X⁶C(O)OR²⁰, —X⁶OC(O)R²⁰, —X⁶NR²⁰R²¹, —X⁶NR²¹C(O)R²⁰, —X⁶NR²¹C(O)OR²⁰, —X⁶C(O) NR²⁰R²¹, —X⁶S(O)₂NR²⁰R²¹, —X⁶NR¹⁹C(O) NR²⁰R²¹ and —X⁶NR²¹C(NR²¹)NR²⁰R²¹, wherein X⁶ is a bond or (C₁₋₆)alkylene, R²⁰ and R²¹ are as defined above;

wherein within R²⁶ any alicyclic or aromatic ring system present may be substituted further by 1 to 5 radicals independently selected from the group consisting of (C₁₋₆)alkyl, (C₁₋₆)alkylidene, cyano, halo, halo-substituted (C₁₋₄)alkyl, nitro, —X⁷NR¹⁴R¹⁴, —X⁷NR¹⁴C(O) OR¹⁴, —X⁷NR¹⁴C(O)NR¹⁴R¹⁴, —X⁷NR¹⁴C(NR¹⁴) NR¹⁴R¹⁴, —X⁷OR¹⁴, —X⁷SR¹⁴, —X⁷C(O)OR¹⁴, —X⁷C(O)NR¹⁴R¹⁴, X⁷S(O)₂NR¹⁴R¹⁴, —X⁷P(O) (OR¹⁴)OR¹⁴, —X⁷OP(O)(OR¹⁴)OR¹⁴, —X⁷NR¹⁴C (O)R$^{15}$, —X$^7$S(O)R$^{15}$, —X$^7$S(O)$_2$R$^{15}$ and —X$^7$C(O)R$^{15}$, wherein X$^7$ is a bond or (C$_{1-6}$) alkylene, and R$^{14}$ and R$^{15}$ are as defined above; or R$^{26}$ together with R$^{27}$ form trimethylene, tetramethylene or phenylene-1,2-dimethylene, optionally substituted with 1 to 3 radicals independently selected from the group consisting of (C$_{1-6}$)alkyl, (C$_{1-6}$)alkylidene, cyano, halo, halo-substituted (C$_{1-4}$)alkyl, nitro, oxo, —X$^8$NR$^{14}$C(O)OR$^{14}$, —X$^8$NR$^{14}$C(O)NR$^{14}$R$^{14}$, —X$^8$NR$^{14}$C(NR$^{14}$)NR$^{14}$R$^{14}$, —X$^8$OR$^{14}$, —X$^8$SR$^{14}$, —X$^8$C(O)OR$^{14}$, —X$^8$C(O)NR$^{14}$R$^{14}$, —X$^8$S(O)$_2$NR$^{14}$R$^1$, —X$^8$R$^{14}$S(O)$_2$ R$^{15}$, —X$^8$P(O)(OR$^{14}$)OR$^{14}$, —X$^8$OP(O)(OR$^{14}$)OR$^{14}$, —X$^8$NR$^{14}$C(O)R$^{15}$, —X$^8$S(O)R$^{15}$, —X$^8$S(O)$_2$R$^{15}$ and —X$^8$C(O)R$^{15}$, wherein X$^8$ is a bond or (C$_{1-6}$)alkylene, R$^{14}$ and R$^{15}$ are as defined above; under coupling reaction conditions to provide a compound of formula (VI):

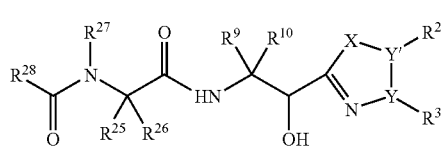
(VI)

where X, Y, Y' , R$^2$, R$^{2a}$, R$^3$, R$^9$, R$^{10}$, R$^{25}$—R$^{28}$ are as defined above;
  (i) optionally protecting the hydroxy group;
  (ii) optionally converting a compound of formula (VI) to an acid addition salt;
  (iii) optionally converting a salt form of a compound of formula (VI) to a free base;
  (iv) optionally separating individual isomers;
  (v) optionally modifying any of the X, Y, R$^2$, R$^3$, R$^9$, R$^{10}$, R$^{25}$—R$^{28}$ groups.

7. The process of claim 6 which further comprises converting a compound of formula (VI) to a compound of formula (VII):

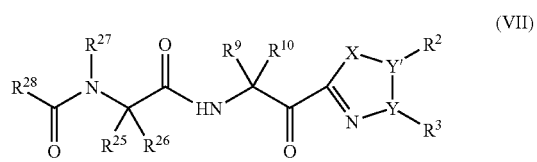
(VII)

where X, Y, Y', R$^2$, R$^{2a}$, R$^3$, R$^9$, R$^{10}$, R$^{25}$—R$^{28}$ are as defined above, with a suitable oxidizing agent; and
  (i) optionally converting a compound of formula (VII) to an acid addition salt;
  (ii) optionally converting a salt form of a compound of formula (VII) to a free base;
  (iii) optionally separating individual isomers; and
  (iv) optionally modifying any of the X, Y, R$^2$, R$^3$, R$^9$, R$^{10}$, R$^{25}$—R$^{28}$ groups.

* * * * *